(12) United States Patent
Allen et al.

(10) Patent No.: US 8,130,095 B2
(45) Date of Patent: Mar. 6, 2012

(54) HEALTH-RELATED SIGNALING VIA WEARABLE ITEMS

(75) Inventors: Paul G. Allen, Seattle, WA (US); Edward S. Boyden, Cambridge, MA (US); Mahalaxmi Gita Bangera, Renton, WA (US); W. Daniel Hillis, Encino, CA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Dennis J. Rivet, Portsmouth, VA (US); Michael A. Smith, Phoenix, AZ (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 754 days.

(21) Appl. No.: 12/231,049

(22) Filed: Aug. 27, 2008

(65) Prior Publication Data

US 2010/0052897 A1   Mar. 4, 2010

(51) Int. Cl.
G08B 1/08 (2006.01)
(52) U.S. Cl. ............ 340/539.12; 340/539.11; 340/573.1
(58) Field of Classification Search ............ 340/539.12, 340/517, 573.1, 539.11; 600/549
See application file for complete search history.

(56) References Cited

U.S. PATENT DOCUMENTS

| | | | |
|---|---|---|---|
| 4,120,294 A | 10/1978 | Wolfe | |
| 5,128,843 A | 7/1992 | Guritz | |
| 5,262,669 A | 11/1993 | Wakatabe et al. | |
| 5,335,313 A | 8/1994 | Douglas | |
| 5,718,247 A | 2/1998 | Frankel | |
| 5,752,512 A | 5/1998 | Gozani | |
| 5,931,764 A * | 8/1999 | Freeman et al. ............ | 482/4 |
| 5,997,472 A | 12/1999 | Bonnell et al. | |
| 5,999,842 A | 12/1999 | Harrison et al. | |
| 6,007,996 A | 12/1999 | McNamara et al. | |
| 6,014,346 A | 1/2000 | Malone | |
| 6,014,626 A | 1/2000 | Cohen | |
| 6,023,637 A | 2/2000 | Liu et al. | |
| 6,067,467 A | 5/2000 | John | |
| 6,126,614 A | 10/2000 | Jenkins et al. | |
| 6,137,527 A | 10/2000 | Abdel-Malek et al. | |
| 6,170,997 B1 | 1/2001 | Glew et al. | |
| 6,177,873 B1 | 1/2001 | Cragun | |
| 6,190,313 B1 | 2/2001 | Hinkle | |
| 6,228,491 B1 | 5/2001 | Antelman | |
| 6,258,576 B1 | 7/2001 | Richards-Kortum et al. | |
| 6,263,243 B1 | 7/2001 | Lang | |
| 6,271,766 B1 | 8/2001 | Didden et al. | |
| 6,275,733 B1 | 8/2001 | Park et al. | |
| 6,277,071 B1 | 8/2001 | Hennessy et al. | |

(Continued)

OTHER PUBLICATIONS

"Exmocare: Answers to Frequently Asked Questions"; Exmocare; printed on Mar. 18, 2008; pp. 1-4; located at: http://www.exmocare.com/faq.

(Continued)

Primary Examiner — Travis Hunnings

(57) ABSTRACT

Systems and methods are described for configuring and using displays, speakers, or other output devices positioned by an article of clothing or other such structure wearable by a healthcare recipient, for example, in a clinic or residential care facility.

39 Claims, 21 Drawing Sheets

U.S. PATENT DOCUMENTS

| | | | |
|---|---|---|---|
| 6,442,241 B1 | 8/2002 | Tsumpes | |
| 6,445,299 B1 | 9/2002 | Rojas, Jr. | |
| 6,490,490 B1 | 12/2002 | Uchikubo et al. | |
| 6,500,630 B2 | 12/2002 | Conover et al. | |
| 6,529,757 B1 | 3/2003 | Patel et al. | |
| 6,529,759 B1 | 3/2003 | Tucker et al. | |
| 6,552,531 B1 | 4/2003 | Fey et al. | |
| 6,569,095 B2 | 5/2003 | Eggers | |
| 6,582,379 B1 | 6/2003 | Stisen | |
| 6,611,846 B1 | 8/2003 | Stoodley | |
| 6,612,982 B1 | 9/2003 | Ouchi | |
| 6,621,918 B1 | 9/2003 | Hu et al. | |
| 6,625,252 B2 | 9/2003 | Mirabella | |
| 6,629,937 B2 | 10/2003 | Watrous | |
| 6,675,040 B1 | 1/2004 | Cosman | |
| 6,699,675 B2 | 3/2004 | Holmes et al. | |
| 6,738,769 B2 | 5/2004 | Sharp | |
| 6,757,412 B1 | 6/2004 | Parsons et al. | |
| 6,785,358 B2 | 8/2004 | Johnson et al. | |
| 6,804,654 B2 | 10/2004 | Kobylevsky et al. | |
| 6,826,578 B2 | 11/2004 | Brackett et al. | |
| 6,834,306 B1 | 12/2004 | Tsimelzon | |
| 6,840,117 B2 | 1/2005 | Hubbard, Jr. | |
| 6,843,771 B2 | 1/2005 | Lo et al. | |
| 6,878,111 B2 | 4/2005 | Kenknight et al. | |
| 6,878,117 B1 | 4/2005 | Watrous | |
| 6,888,502 B2 | 5/2005 | Beigel et al. | |
| 6,907,375 B2 | 6/2005 | Guggari et al. | |
| 6,934,579 B2 | 8/2005 | Mantzaridis et al. | |
| 6,942,626 B2 | 9/2005 | Salisbury et al. | |
| 6,944,497 B2 | 9/2005 | Stypulkowski | |
| 6,963,772 B2 | 11/2005 | Bloom et al. | |
| 6,968,294 B2 | 11/2005 | Gutta et al. | |
| 6,990,455 B2 | 1/2006 | Vozick et al. | |
| 7,003,525 B1 | 2/2006 | Horvitz et al. | |
| 7,016,467 B2 | 3/2006 | Brooks | |
| 7,016,601 B1 | 3/2006 | Yoneya et al. | |
| 7,020,666 B2 | 3/2006 | Doise et al. | |
| 7,037,273 B2 | 5/2006 | Zhu et al. | |
| 7,076,436 B1 | 7/2006 | Ross, Jr. et al. | |
| 7,079,035 B2 | 7/2006 | Bock et al. | |
| 7,149,645 B2 | 12/2006 | Mangrulkar et al. | |
| 7,155,281 B1 | 12/2006 | Fayram | |
| 7,158,861 B2 | 1/2007 | Wang et al. | |
| 7,180,415 B2 | 2/2007 | Bankert et al. | |
| 7,184,580 B2 | 2/2007 | Hamid | |
| 7,190,987 B2 | 3/2007 | Lindekugel et al. | |
| 7,204,425 B2 | 4/2007 | Mosher, Jr. et al. | |
| 7,208,983 B2 | 4/2007 | Imaizumi et al. | |
| 7,209,955 B1 | 4/2007 | Major et al. | |
| 7,226,426 B2 | 6/2007 | Thomson | |
| 7,233,781 B2 | 6/2007 | Hunter et al. | |
| 7,242,807 B2 | 7/2007 | Waupotitsch | |
| 7,250,855 B2 | 7/2007 | Suenbuel et al. | |
| 7,254,425 B2 | 8/2007 | Lowery et al. | |
| 7,257,531 B2 | 8/2007 | Holub | |
| 7,263,688 B2 | 8/2007 | Pitzel et al. | |
| 7,269,718 B2 | 9/2007 | Alexander, III et al. | |
| 7,280,992 B2 | 10/2007 | Nitz | |
| 7,286,877 B2 | 10/2007 | Daum | |
| 7,289,883 B2 | 10/2007 | Wang et al. | |
| 7,291,111 B2 | 11/2007 | Shertukde et al. | |
| 7,296,238 B1 | 11/2007 | Zurawski | |
| 7,308,246 B2 | 12/2007 | Yamazaki et al. | |
| 7,310,564 B2 | 12/2007 | Leyerer et al. | |
| 7,310,615 B2 | 12/2007 | Lewis | |
| 7,313,529 B2 | 12/2007 | Thompson | |
| 7,317,821 B2 | 1/2008 | Chen et al. | |
| 7,317,955 B2 | 1/2008 | McGreevy | |
| 7,325,054 B2 | 1/2008 | Ishimoto | |
| 7,325,297 B2 | 2/2008 | Xia | |
| 7,327,861 B2 | 2/2008 | Choshi et al. | |
| 7,331,667 B2 | 2/2008 | Grotehusmann et al. | |
| 7,332,743 B2 | 2/2008 | Yang et al. | |
| 7,333,014 B2 | 2/2008 | Agrawal et al. | |
| 7,340,077 B2 | 3/2008 | Gokturk et al. | |
| 7,340,293 B2 | 3/2008 | McQuilkin | |
| 7,343,305 B2 | 3/2008 | Benn et al. | |
| 7,346,205 B2 | 3/2008 | Walker, Jr. | |
| 2002/0032386 A1 | 3/2002 | Sackner et al. | |
| 2002/0127623 A1 | 9/2002 | Minshull et al. | |
| 2003/0135127 A1 | 7/2003 | Sackner et al. | |
| 2003/0174049 A1 | 9/2003 | Beigel et al. | |
| 2004/0039254 A1 | 2/2004 | Stivoric et al. | |
| 2004/0064169 A1 | 4/2004 | Briscoe et al. | |
| 2004/0106163 A1 | 6/2004 | Workman, Jr. et al. | |
| 2004/0138568 A1 | 7/2004 | Lo et al. | |
| 2005/0148842 A1 | 7/2005 | Wang et al. | |
| 2005/0154277 A1 | 7/2005 | Tang et al. | |
| 2005/0192845 A1 | 9/2005 | Brinsfield et al. | |
| 2005/0228234 A1* | 10/2005 | Yang | 600/300 |
| 2005/0245839 A1* | 11/2005 | Stivoric et al. | 600/549 |
| 2005/0270158 A1 | 12/2005 | Corbett, Jr. | |
| 2006/0036472 A1 | 2/2006 | Crockett | |
| 2006/0154642 A1* | 7/2006 | Scannell | 455/404.1 |
| 2006/0218626 A1 | 9/2006 | Goehler | |
| 2006/0218837 A1 | 10/2006 | Riley | |
| 2006/0253107 A1 | 11/2006 | Hashimshony et al. | |
| 2006/0290526 A1 | 12/2006 | Golson | |
| 2007/0020181 A1 | 1/2007 | Workman et al. | |
| 2007/0032739 A1 | 2/2007 | Hashimshony et al. | |
| 2007/0032747 A1 | 2/2007 | Hashimshony et al. | |
| 2007/0076407 A1 | 4/2007 | Marmaropoulos | |
| 2007/0185390 A1 | 8/2007 | Perkins et al. | |
| 2007/0199137 A1 | 8/2007 | Numes Ramos De Carvalho et al. | |
| 2007/0200863 A1 | 8/2007 | Guzman | |
| 2007/0279852 A1* | 12/2007 | Daniel et al. | 361/683 |
| 2007/0299325 A1* | 12/2007 | Farrell et al. | 600/301 |
| 2008/0110069 A1 | 5/2008 | McDermott et al. | |
| 2008/0143080 A1 | 6/2008 | Burr | |
| 2008/0147231 A1* | 6/2008 | Fernandez | 700/138 |

OTHER PUBLICATIONS

"Exmocare: BT2"; Exmocare; printed on Mar. 18, 2008; pp. 1-5; located at: http://www.exmocare com/bt2/.

"MiniLink Real-Time Transmitter"; Medtronic; pp. 1-3; printed on Aug. 20, 2008; located at: http://www.minimed.com/products/insulinpumps/components/minilink.html.

"News on Your Wrist"; Cyberjournalist.net—Online News Association; p. 1; located at: http://www.cyberjournalist.net/news/000959.php, Feb. 9, 2004.

"Premium Equipment: PRO TECH Smart GPS Tracking System"; King Monitoring Services, Inc.; printed on Aug. 20, 2008; pp. 1-2; located at: http://www.kingmonitoring.com/KingMonitoringServices_pr.htm.

* cited by examiner

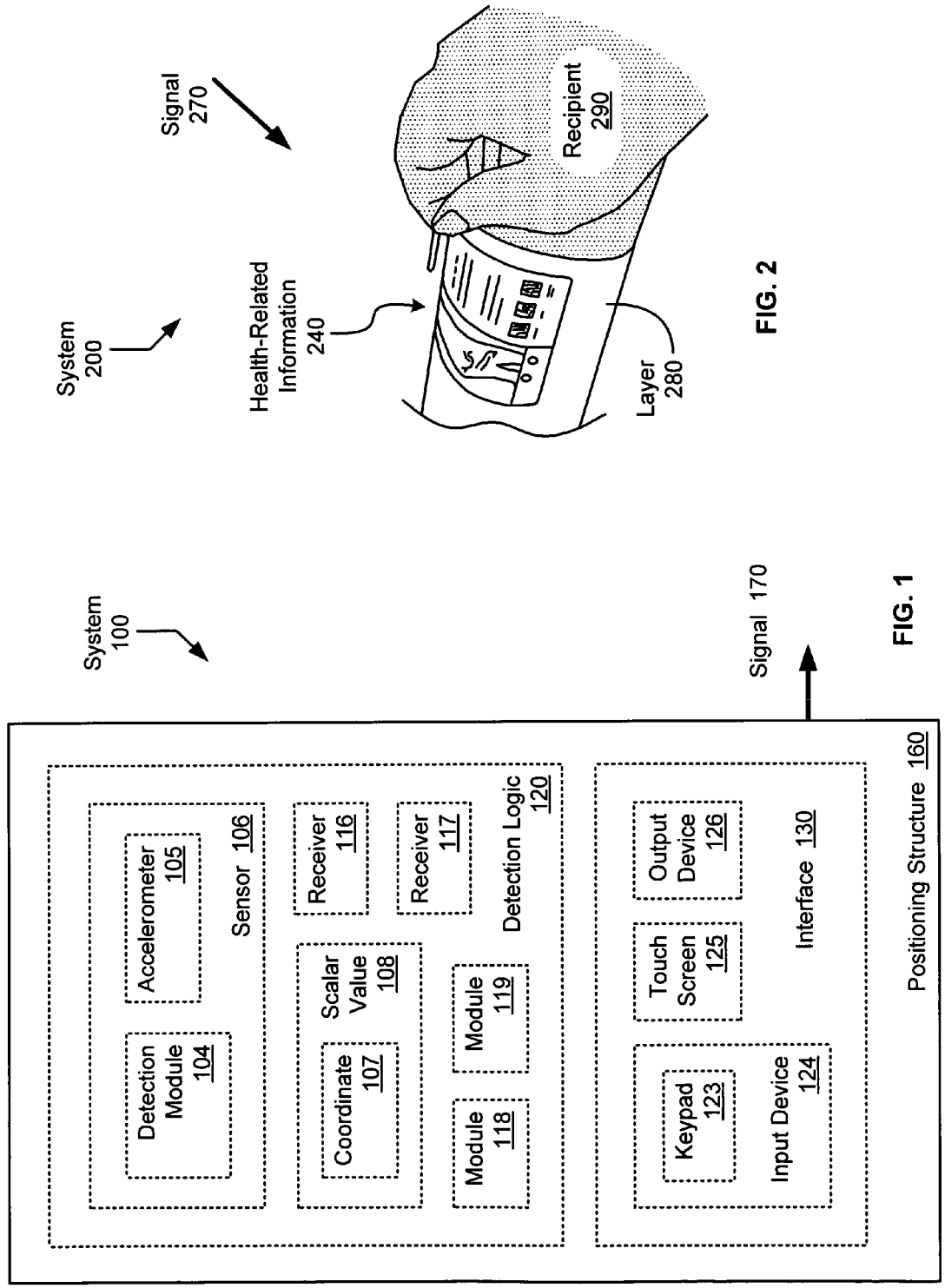

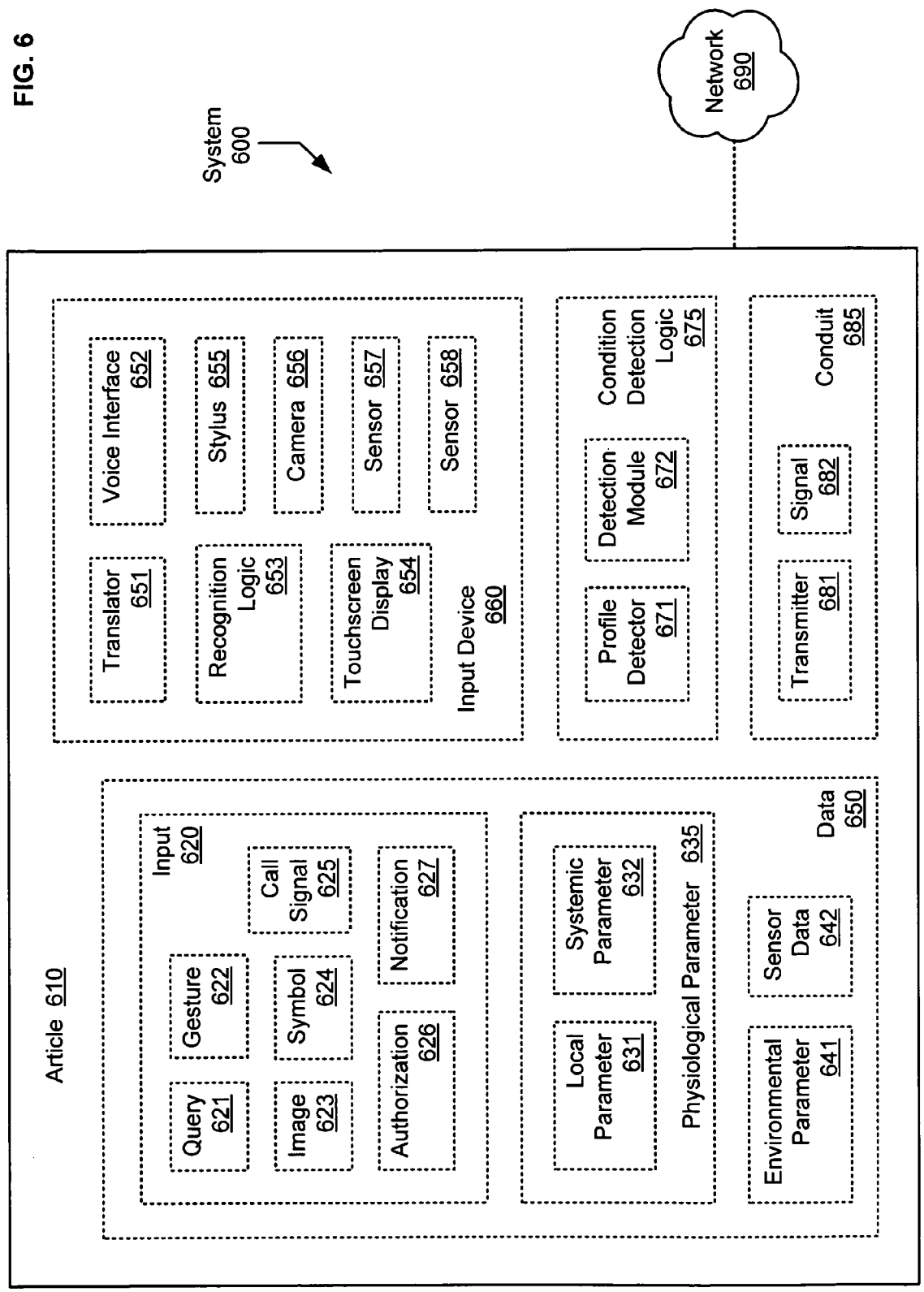

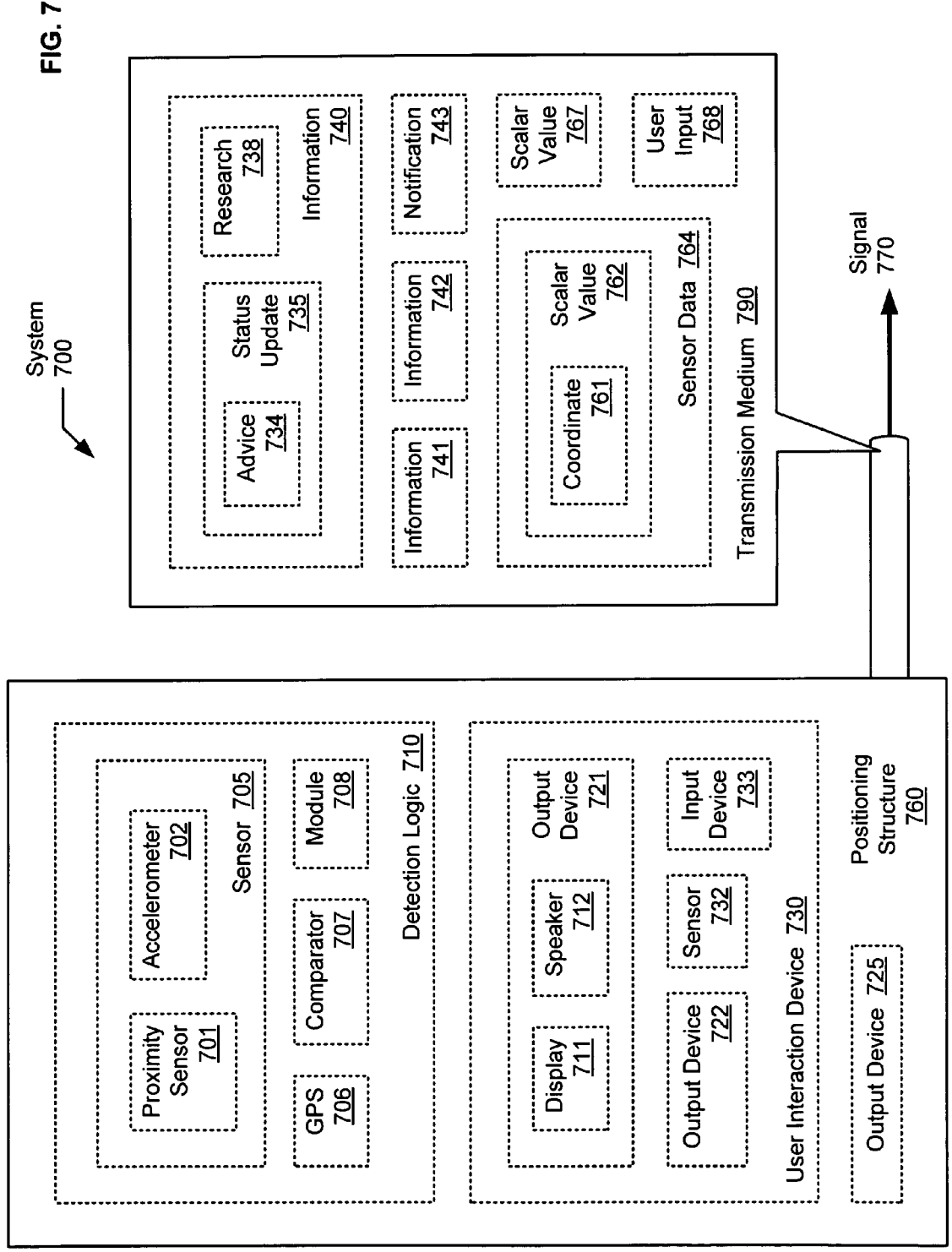

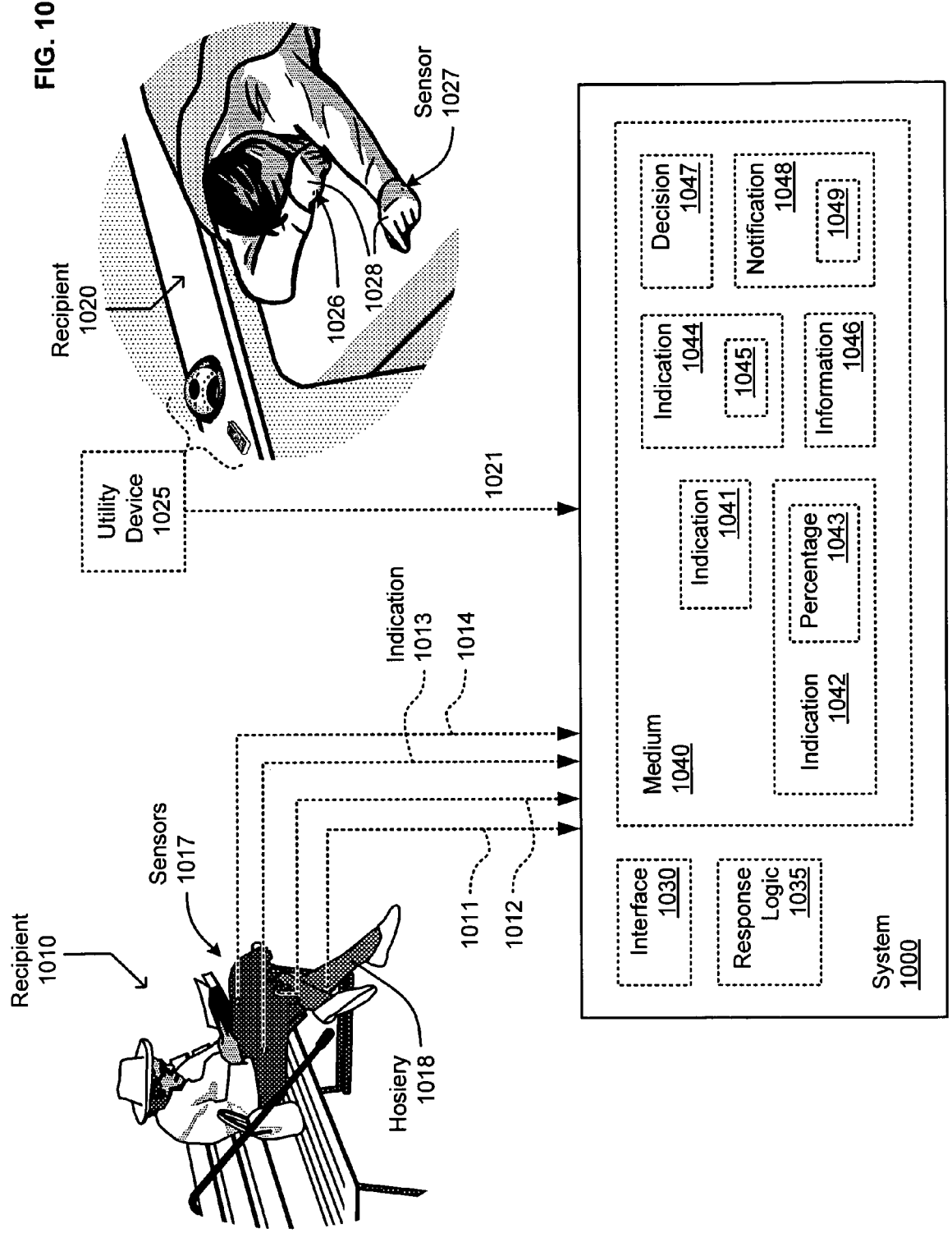

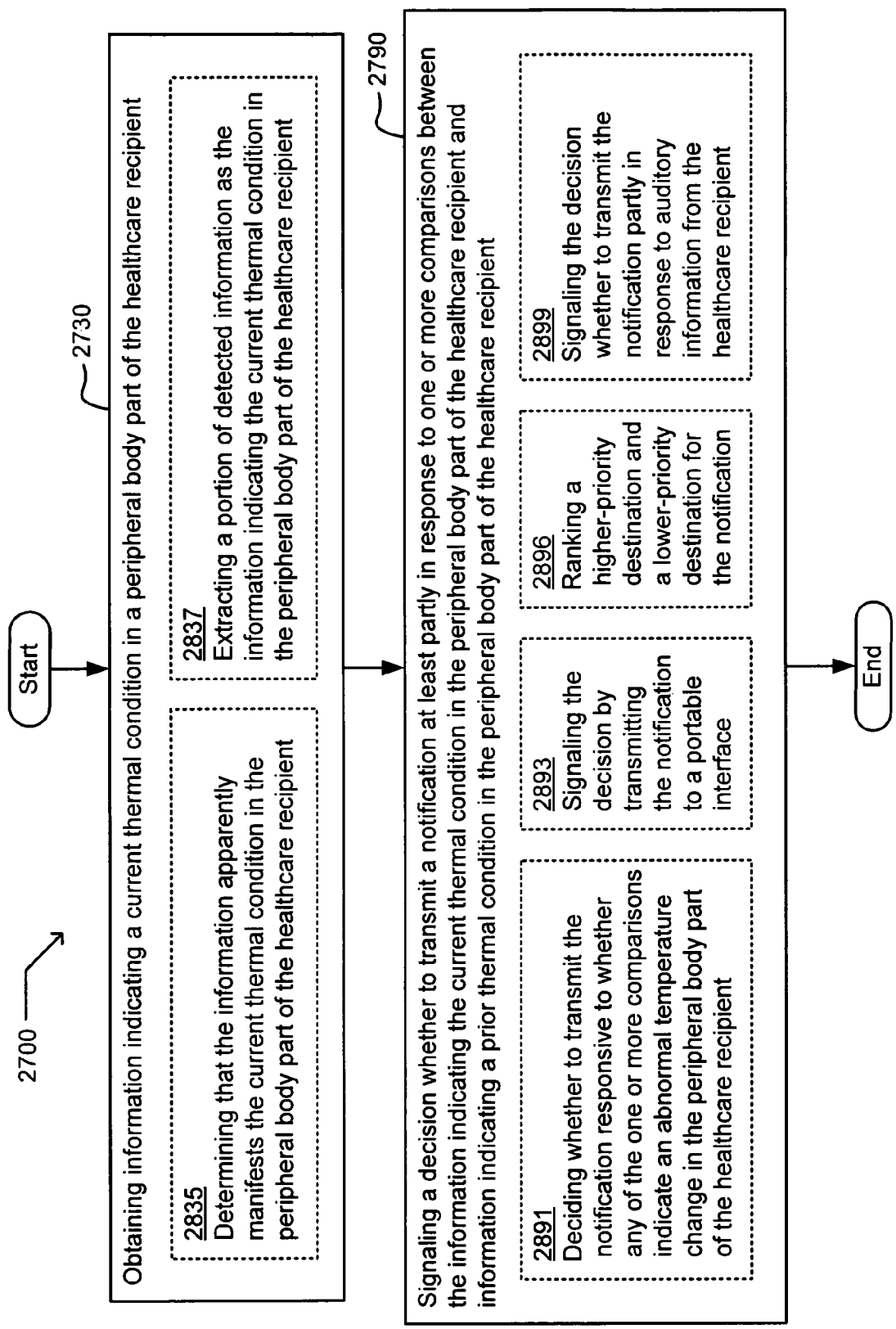

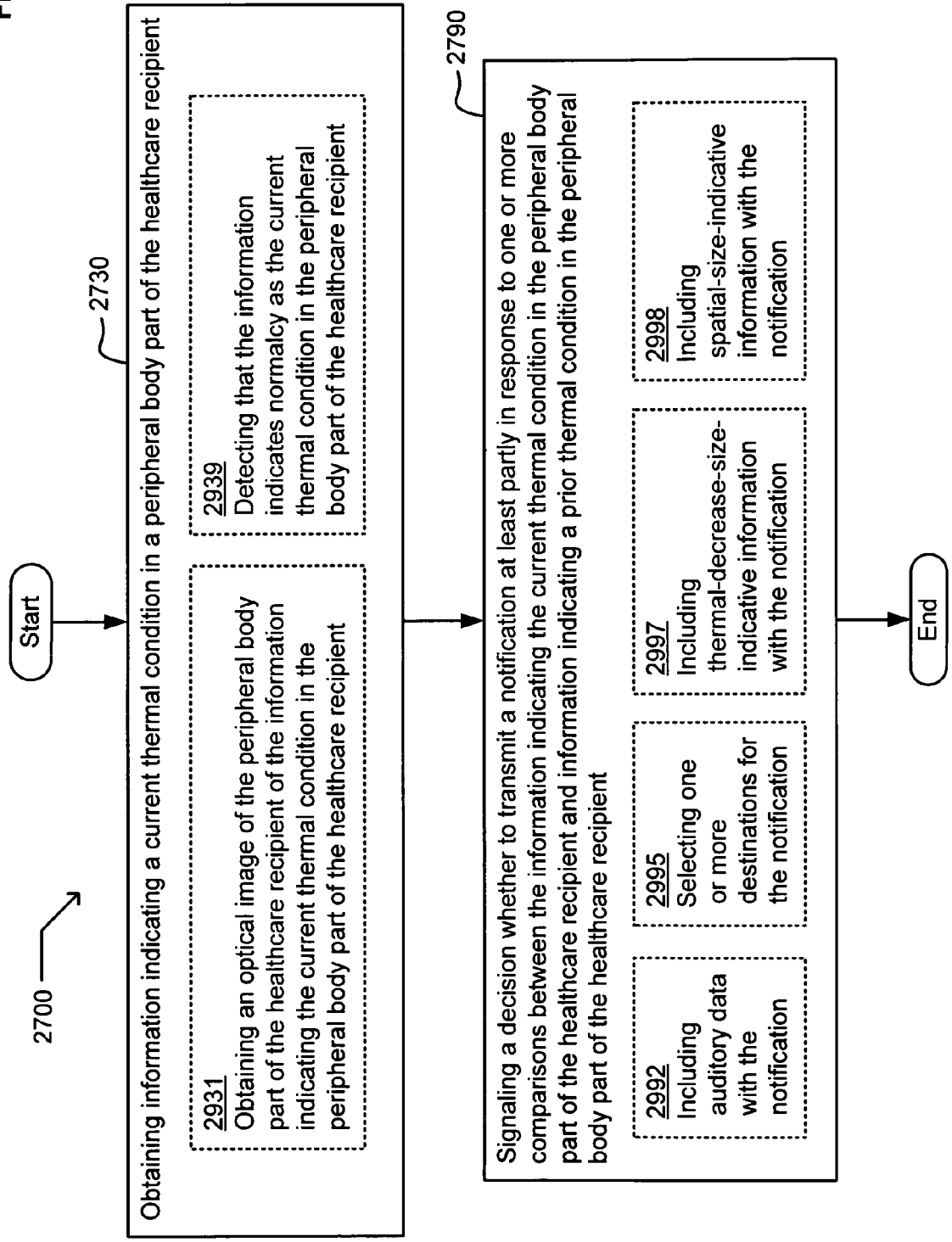

HEALTH-RELATED SIGNALING VIA WEARABLE ITEMS

SUMMARY

In one aspect, a method includes but is not limited to obtaining information indicating a current thermal condition in a peripheral body part of the healthcare recipient and signaling a decision whether to transmit a notification at least partly in response to one or more comparisons between the information indicating the current thermal condition in the peripheral body part of the healthcare recipient and information indicating a prior thermal condition in the peripheral body part of the healthcare recipient. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining information indicating a current thermal condition in a peripheral body part of the healthcare recipient and circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient. In addition to the foregoing, other system aspects are described in the claims, drawings, and text forming a part of the present disclosure.

In one aspect, a system includes but is not limited to a positioning structure configured to be worn by a healthcare recipient; a receiver supported by the positioning structure and configured to receive a wireless signal; and a user interaction device supported by the positioning structure and configured to present at least some health-related information in a vicinity of the healthcare recipient responsive to the wireless signal.

In one aspect, a system includes but is not limited to a positioning structure configured to be worn by a healthcare recipient; a receiver supported by the positioning structure and configured to receive a wireless signal; and an output device supported by the positioning structure and configured to transmit at least some health-related information responsive to the wireless signal and to sensor data in proximity to the healthcare recipient.

In one aspect, a system includes but is not limited to a positioning structure configured to be worn by a healthcare recipient; a receiver supported by the positioning structure and configured to receive a wireless signal; and a first output device supported by the positioning structure and configured to transmit at least some health-related information responsive to the wireless signal and to a status update relating to the healthcare recipient.

In one aspect, a system includes but is not limited to a positioning structure configured to be worn by a healthcare recipient; a first output device supported by the positioning structure and configured to transmit at least some health-related information in a vicinity of the healthcare recipient; and a second output device supported by the positioning structure and configured to transmit a wireless signal containing one or more scalar values indicating a position of the healthcare recipient.

In one aspect, a system includes but is not limited to a positioning structure configured to be worn by a healthcare recipient; a movement detector supported by the positioning structure; a first output device supported by the positioning structure and configured to transmit at least a signal from the movement detector; and a second output device supported by the positioning structure and configured to transmit at least some health-related information in a vicinity of the healthcare recipient.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1-26 depict exemplary environments in which one or more technologies may be implemented.

FIGS. 28-29 depict variants of the flow of FIG. 27.

DETAILED DESCRIPTION

Figure 3:
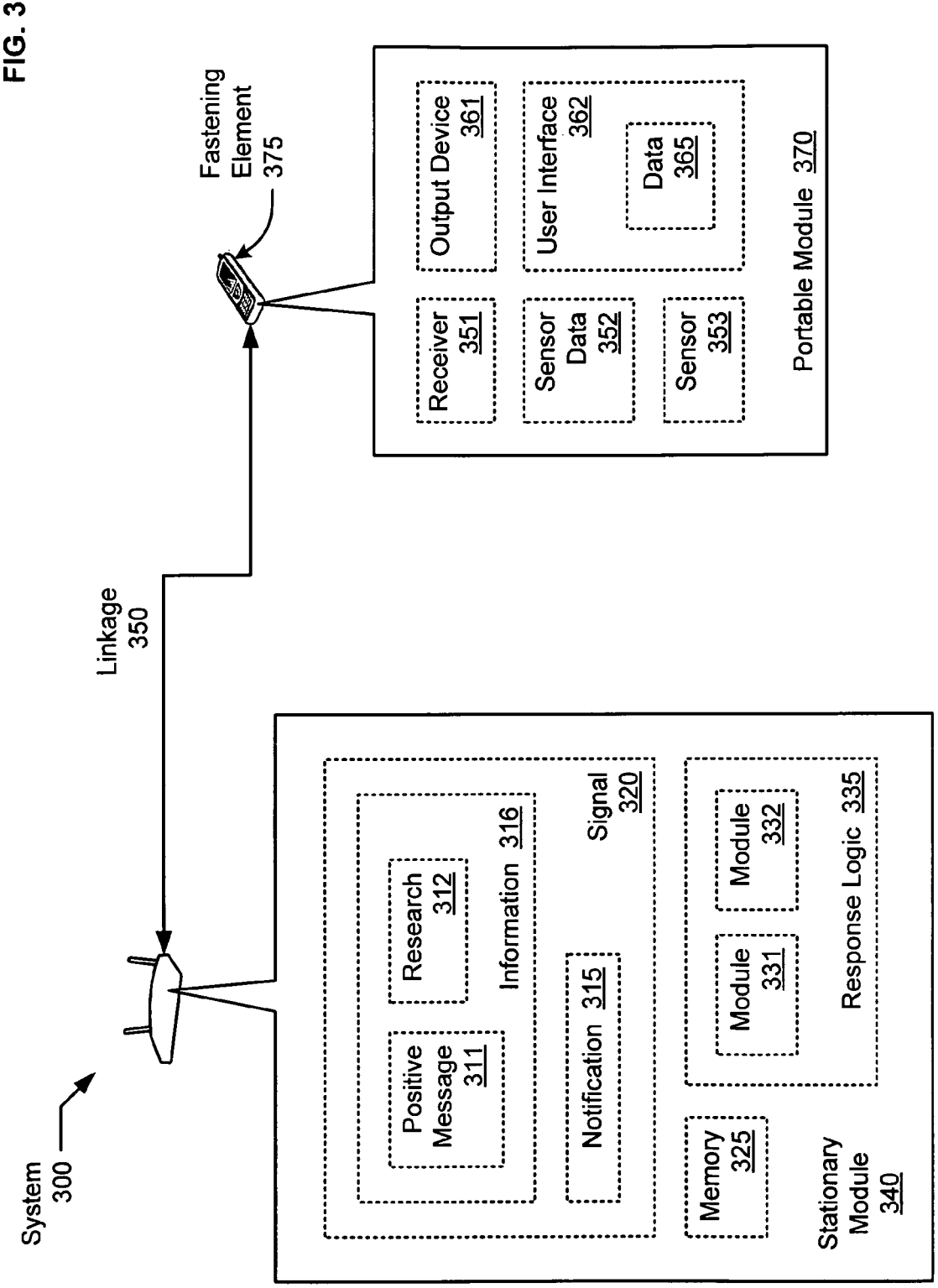

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With reference now to FIG. 1, shown is a system 100 in which one or more technologies may be implemented. System 100 may include a wearable interface or other positioning structure 160 effective for positioning instances of detection logic 120, devices 130 for transmitting signals 170 about a physiological or other health issue, or other components near a healthcare recipient. Detection logic 120 may include one or more instances of symptom or event detection modules 104, accelerometers 105, or other sensors 106; positional coordinates 107 or other scalar values 108; or receivers 116, 117 or other modules 118, 119. Interface 130 may include one or more keypads 123 or other input devices 124, touchscreens 125, or other input or output devices 126.

With reference now to FIG. 2, shown is a system 200 comprising a sleeve, wrap, cuff, or other such layer 280 wearable by a healthcare recipient 290 and configured to present health-related information 240 obtained from or otherwise responsive to radio frequency or other signals 270. In some contexts, layer 280 may implement a positioning structure like that of FIG. 1.

A first embodiment provides (a) wearable display layer 280 or other positioning structure 160 and (b) one or more touch screens 125 or other input and/or output devices supported by the positioning structure 160 and configured to present medication reminders, procedural explanations, scheduling data, or other health-related information 240 in a vicinity of a healthcare recipient 290. In some variants, one or more output devices 126 may likewise be supported by the positioning structure 160 and configured to transmit a wireless or other signal 170 containing a distance measurement or other scalar value 108 indicating a past or current position of the healthcare recipient.

Another embodiment provides a positioning structure 160 configured to be worn by a healthcare recipient 290, one or more receivers 117 supported by the positioning structure 160 and configured to receive a wireless or other signal 270, and one or more output devices 126 supported by the positioning structure 160 and configured to present a scalar value 108 or other health-related information 240 responsive to signal 270 and to one or more status updates (from a sensor 106, another receiver 116, or other input devices, e.g.) relating to healthcare recipient 290.

Yet another embodiment provides a positioning structure 160 configured to be worn by a healthcare recipient 290, one or more receivers 116, 117 supported by the positioning structure 160 and configured to receive signal 270, and one or more touch screens 125 or other user interaction devices 130 supported by the positioning structure 160 and configured to present a care provider's location, a prescription status, or other health-related information 240 in a vicinity of the healthcare recipient 290 responsive to signal 270. Other such embodiments are described below with reference to FIGS. 3-26.

With reference now to FIG. 3, shown is a system 300 comprising one or more wireless modems or other such stationary modules 340 operable for communicating via linkage 350 with a wearable handset or other such portable module 370. Stationary module 340 may include memory 325 or one or more modules 331, 332 of response logic 335 configured to handle one or more signals 320 comprising health-related information 316 and/or other notifications 315. In some contexts, for example, such signals may include parametric improvements or other such positive messages 311, medical research 312, updates, explanations, responses to inquiries, or other such data 365 suitable for presentation (via user interface 362, e.g.) to a healthcare recipient. Portable module 370 may include one or more transceivers or other receivers 351, sensors 353 for obtaining measurements or other sensor data 352, or output devices 361 as described herein.

An embodiment provides a positioning structure or other portable module 370 configured to be worn by a healthcare recipient; one or more receivers 351 supported by the positioning structure and configured to receive a wireless or other signal 320 such as positive messages 311, reminders, research 312, or other health-related information 316; and at least one user interface 362 or other output device 361 supported by the positioning structure and configured to transmit at least some of the health-related or other data responsive to the signal 320 and to sensor data 352 from one or more sensors 353 in proximity to the healthcare recipient. In some contexts, such modules may include a hook, clip, adhesive backing, or other fastening element 375 effectively permitting the module to be worn by the healthcare recipient. Other such embodiments are described below with reference to FIGS. 4-26.

Figure 4:
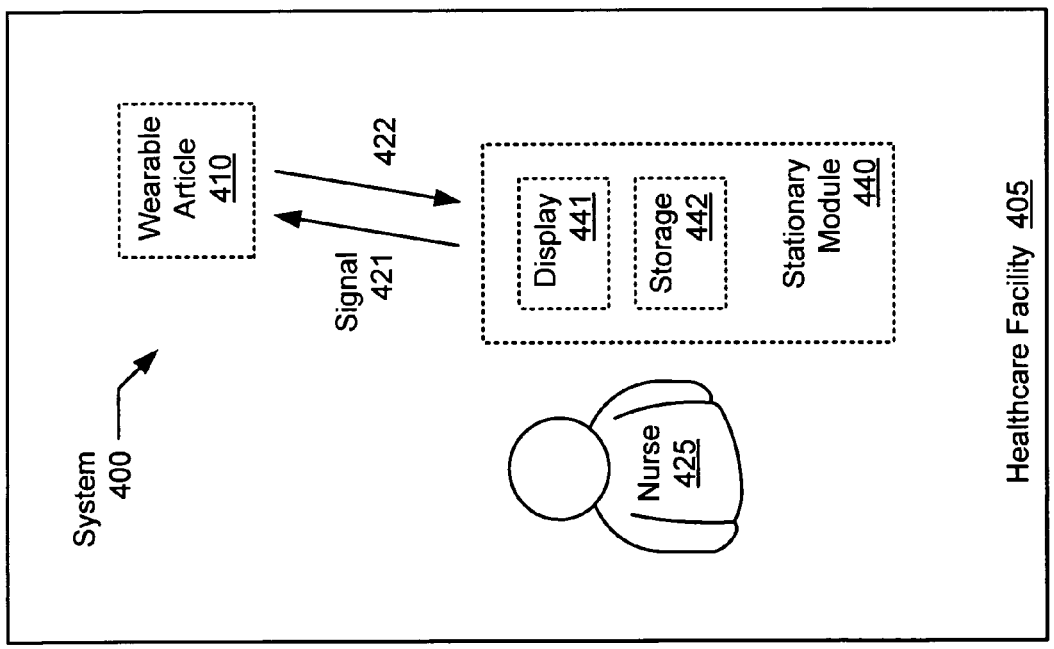

With reference now to FIG. 4, shown is a system 400 in which one or more technologies may be implemented. System 400 may include one or more instances of wearable articles 410 configured to transmit and/or receive signals 421, 422 (handled by stationary module 440, for example) in a healthcare facility 405. In some contexts, such modules may include one or more displays 441 (viewable by a nurse 425, e.g.), interfaces, and/or storage 442 configured to retain selected components of such signals 421, 422.

Figure 5:
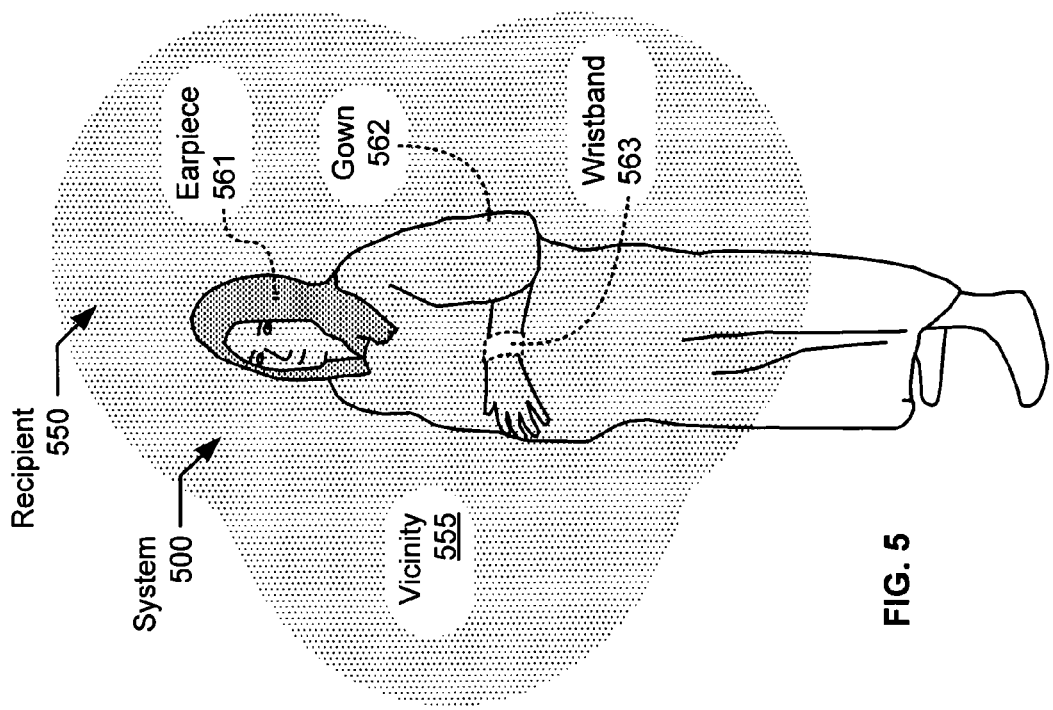

With reference now to FIG. 5, shown is a system 500 comprising one or more instances of an earpiece 561, gown 562, wristband 563, or other such structures effective for positioning one or more modules configured to communicate in a vicinity 555 of a healthcare recipient 550 who wears the structure(s). Other such embodiments are described herein, optionally configured to communicate with a stationary or other module and/or to include one or more sensors for detecting status indicia relating to healthcare recipient 550.

An embodiment provides a positioning structure 160 configured to be worn by a healthcare recipient 550, one or more sensors 106 or other detection logic 120 supported by the positioning structure 160, one or more output devices 126 supported by the positioning structure 160 and configured to transmit at least a signal 170 from the detection logic 120, and one or more other devices 130 supported by the positioning structure 160 and configured to present at least some health-related information 240 in a vicinity 555 of the healthcare recipient 550. Other such embodiments are described below with reference to FIGS. 6-26.

With reference now to FIG. 6, shown is a system 600 in which one or more technologies may be implemented comprising wearable or other articles 610 operable for handling communications to and/or from one or more networks 690. In some variants, such articles may include one or more instances of data 650; input devices 660; profile detectors 671, detection modules 672, or other condition detection logic 675; or transmitters 681 or other conduits 685 operable for bearing one or more signals 682. Data 650 may include one or more queries 621, gestures 622, images 623, symbols 624, call signals 625, authorizations 626, notifications 627, or other such input 620; local parameters 631, systemic parameters 632, or other physiological parameters 635 relating to a healthcare recipient; or environmental parameters 641 or other sensor data 642 as described herein. Input device 660 may include one or more instances of translators 651, voice interfaces 652, recognition logic 653, touchscreen displays 654 (optionally operable with a stylus 655, e.g.), cameras 656, or other sensors 657, 658.

An embodiment provides a positioning structure configured to be worn by a healthcare recipient 550, one or more conduits 685 or other receivers supported by a positioning structure (such as an article 610 wearable by a healthcare recipient 550) and configured to receive a wireless or other signal 682, and one or more input devices 660 supported by the positioning structure and configured to transmit at least some physiological parameters 635 or other health-related information in a vicinity 555 of the healthcare recipient responsive to signal 682 (from network 690, e.g.).

In some variants, an earpiece 561, gown 562, wristband 563 or other positioning structure for in-patient care exclusively supports institutional broadcasts or other content controlled by and/or provided in a healthcare facility 405. Alternatively or additionally, such wearable articles 410 or other positioning structures may (optionally) include or otherwise interact with sensors or other components effectively permitting use by or other interaction with the healthcare recipient. Such structures may, for example, support one or more voice interfaces 652, a stylus 655, or other input devices 660 configured to permit user input from the healthcare recipient 550.

With reference now to FIG. 7, shown is a system 700 in which one or more technologies may be implemented. Positioning structure 760 may include or otherwise position one or more instances of sensors 705, global positioning systems 706, comparators 707, or other such modules 708 of detection logic 710. Such sensors may include one or more proximity sensors 701, accelerometers 702, or other components described, for example, below with reference to FIGS. 14-17. Such a positioning structure may further include one or more displays 711, speakers 712, or other output devices 721, 722; sensors 732; or input devices 733 to permit interactions with a healthcare recipient (via user interaction device 730, e.g.). Such positioning structures may likewise include one or more output devices 725 operably coupled with one or more antennas or other energy transmission media 790. Such media may transmit advice 734, status updates 735, research 738, or other information 740, 741, 742 or other notifications 743; coordinates 761, scalar values 762, 767, sensor data 764, or user input 768 as described herein, optionally as signal 770.

An embodiment provides a positioning structure 760 configured to be worn by a healthcare recipient, an accelerometer 702 or other such detection logic 710 operable for detecting movement and supported by the positioning structure 760, one or more output devices 725 supported by the positioning structure 760 and configured to transmit wireless or other signals 770 from the detection logic 710, and one or more output devices 721 supported by the positioning structure 760 and configured to present at least some health-related information in a vicinity of the healthcare recipient. This can occur, for example, in a context in which such circuitry implements or otherwise interacts with one or more local modules (of FIGS. 11-17, e.g.) within, on, or near the healthcare recipient.

An embodiment provides a garment or other positioning structure 760 configured to be worn by a healthcare recipient 550, one or more output devices 721, 725 supported by the positioning structure 760 and configured to present at least some health-related information in a vicinity of the healthcare recipient 550; and one or more output devices 722, 725 supported by the positioning structure 760 and configured to transmit signal 770 containing one or more coordinates 761 or other scalar values 762, 767 indicating a (past or current) position of the healthcare recipient 550. In some contexts, for example, output device 725 may include one or more light emitting diodes, powered displays, or other device-readable energy transmission media 790.

Figure 8:
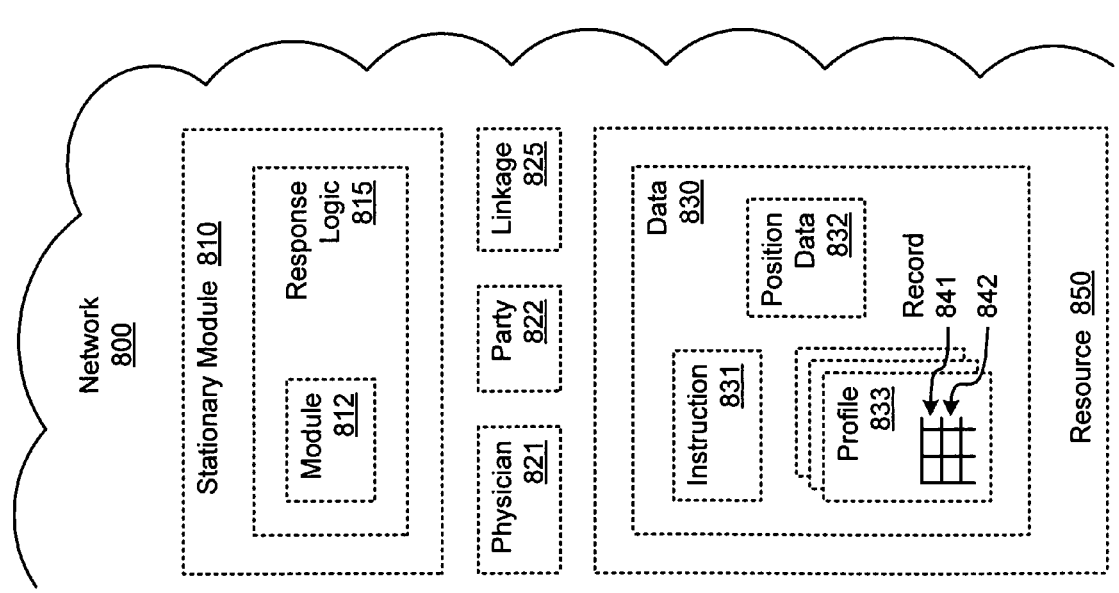

With reference now to FIG. 8, shown is a network 800 comprising one or more stationary modules 810 or other facilities for interacting with physicians 821 or other parties 822 or resources 850 via linkages 825. In some contexts, for example, such stationary modules may include one or more modules 812 of response logic 815. Such resources may include one or more instructions 831, position data 832, or records 841, 842 comprising profiles 833 as described herein.

In some variants, for example, a regional call center or other such service may maintain numerous interaction profiles 833 or other configuration data 830 continually in response to telephonic or other incoming requests. Healthcare recipients or small healthcare facilities may, for example, use such data and/or devices to facilitate interactions with patient monitoring data aggregation, consultation, research assistance, resource referral, or other such telemedicine and related online services. Alternatively or additionally, one or more modules 812 of response logic 815 may respond to such events or other conditions by transmitting the notification(s) to an interested party 822 and/or other selective destinations identified in record 841. Other such embodiments are described, for example, below with reference to FIGS. 9-26.

Figure 9:
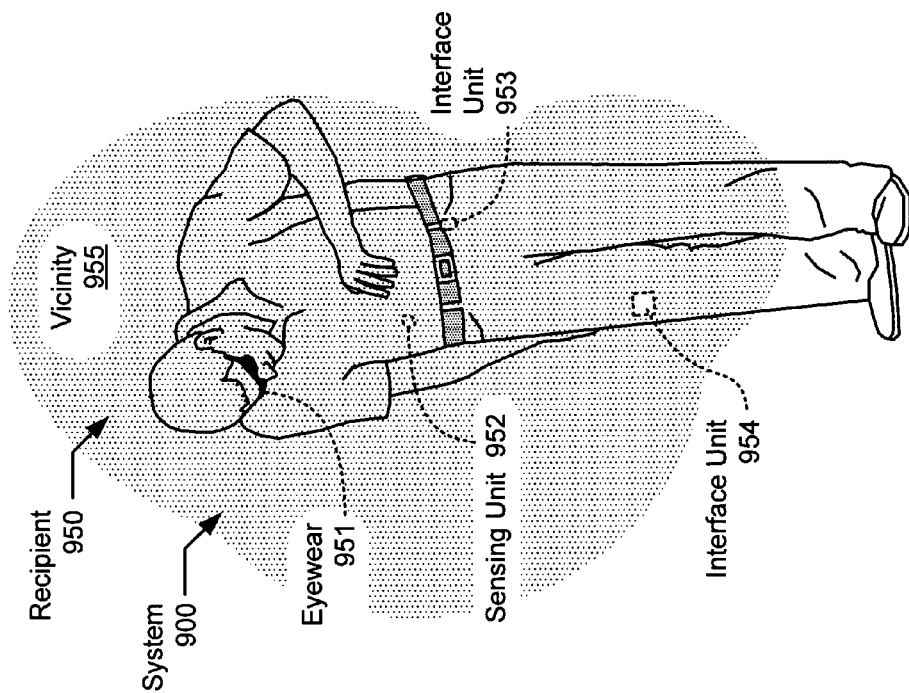

With reference now to FIG. 9, shown is a system 900 comprising one or more instances of eyewear 951, sensing units 952, interface units 953, 954, or other such structure(s) effective for positioning one or more modules configured to communicate in a vicinity 955 of a healthcare recipient 950 who wears the structure(s). Other such embodiments are described herein, optionally configured to communicate with a stationary or other module and/or to include one or more sensors for detecting status indicia relating to healthcare recipient 950.

An embodiment provides special-purpose eyewear 951, one or more sensing units 952 or interface units 953, 954, or other such positioning structures configured to be worn by a healthcare recipient 950; one or more output devices 361 supported by the positioning structure and configured to transmit at least some positive messages 311 or other health-related data 365 (optionally interspersed with notifications 315 or other information) in a vicinity 955 of the healthcare recipient 950; and one or more output devices 361 supported by the positioning structure and configured to transmit a wireless or other signal containing one or more coordinates 761 or other scalar values 762 indicating a (past or current) position of the healthcare recipient 950.

In some variants, a nurse 425 or other party 822 can use a stationary module 440 or other linkage 825 to transmit one or more instructions 831 to configure a recipient-specific interaction profile 833 containing one or more records 841, 842 associating a medical or other condition with one or more notifications 315, for example, to be delivered via output device 361 and/or in a vicinity 555, 955 of the healthcare recipient(s) or other subscribers.

With reference now to FIG. 10, shown is a system 1000 in which one or more technologies may be implemented. System 1000 may be positioned centrally or local to healthcare recipients 1010, 1020, for example, and/or configured to invoke one or more interfaces 1030 or other response logic 1035 in response to one or more indications 1011, 1012, 1013, 1014, 1021 from sensors 1017, 1026, 1027 in, on, or near extremities 1028 or other body parts of interest. This can occur, for example, in a context in which hosiery 1018, clothing, or one or more stationary or other utility devices 1025 within a detection range of sensors 1017, 1026, 1027 implements or otherwise interacts with system 1000. In some embodiments, such sensors may be implanted in a body tissue of interest or in a structure with which healthcare recipients 1010, 1020 may interact. Alternatively or additionally, some such sensors may be worn as clothing, a support, a patch, a bandage, a watch, or some other article in the healthcare recipients' vicinity. Such articles may (optionally) include one or more instances of wearable display or other storage or communication media 1040 configured to bear one or more percentages 1043 or other health indications 1041, 1042, 1044 such as content 1045; information 1046; decisions 1047; or notifications 1048 containing content 1049, for example, in flows as described below.

In some variants, one or more modules 332 of response logic 335, 815, 1035 are configured to cause one or more notifications 315 to be routed locally to one or more speakers or other output devices 361 in a vicinity 555, 955 of a healthcare recipient 550, 950. Alternatively or additionally, such systems may include one or more utility devices 1025, wearable sensors 1017, 1027, or other such modules configured to process, present, or otherwise handle raw or other current sensor data as described herein.

Figure 11:
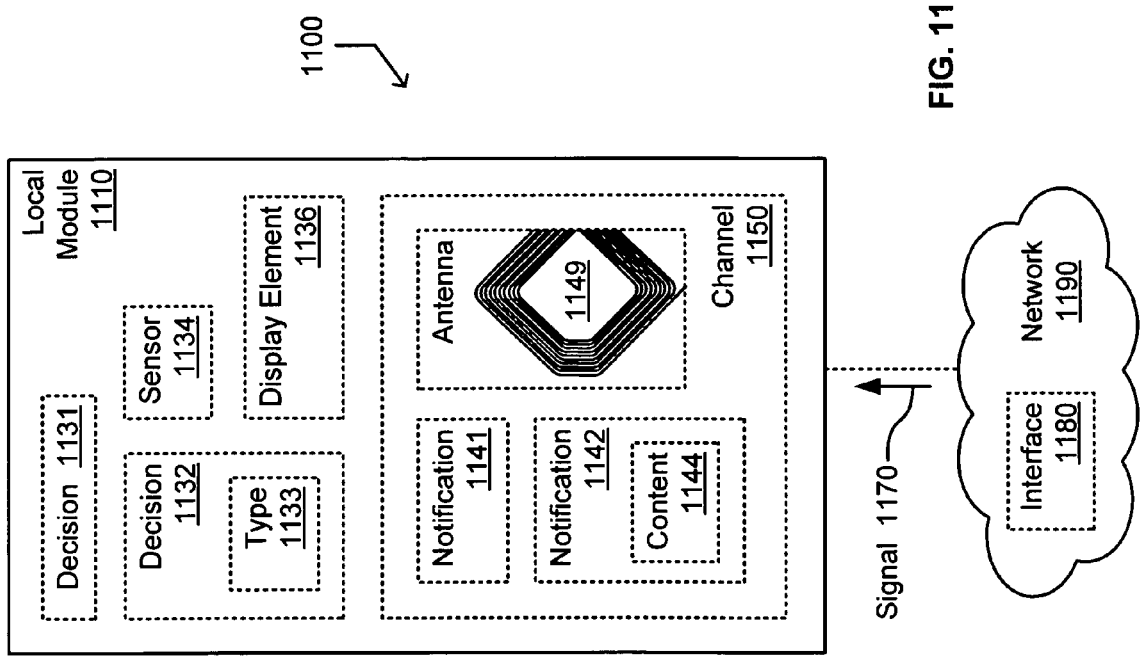

With reference now to FIG. 11, shown is a system 1100 in which one or more technologies may be implemented comprising one or more local modules 1110 operably coupled with one or more interfaces 1180 in a network 1190. Local module 1110 may handle or otherwise include one or more decisions 1131, 1132 of various types 1133, sensors 1134, display elements 1136, or channels 1150 operable for triggering or transmitting one or more notifications 1141, 1142 such as content 1144, optionally via one or more radio-frequency or other antennas 1149. Such antennas may be used in an implanted or other portable article, for example, as described throughout this document.

In some variants, such notification logic may be configured to provide timely information or advice to one or more individuals in a healthcare recipient's vicinity. Other such embodiments are described, for example, with reference to FIGS. 1-10. Alternatively or additionally, one or more such network components may include media configured for display: flat screen displays, image-projecting devices, touch screens, or other such display media.

An embodiment provides a local module 1110 or other positioning structure configured to be worn by a healthcare recipient, one or more antennas 1149 or other receivers supported by the positioning structure and configured to receive a wireless or other signal 1170, and one or more display elements 1136 or other output devices supported by the positioning structure and configured to present one or more options, decisions 1131, 1132, or other health-related information responsive to signal 1170 and to one or more status updates (from a sensor 1134 or other input device 660, e.g.) relating to the healthcare recipient. This can occur, for example, in a context in which local module 1110 and/or network 1190 includes one or more components or instances of article 610. Alternatively or additionally, in some variants, such circuitry can implement or otherwise interact with one or more local modules (of FIGS. 11-17, e.g.) within, on, or near the healthcare recipient.

Figure 12:
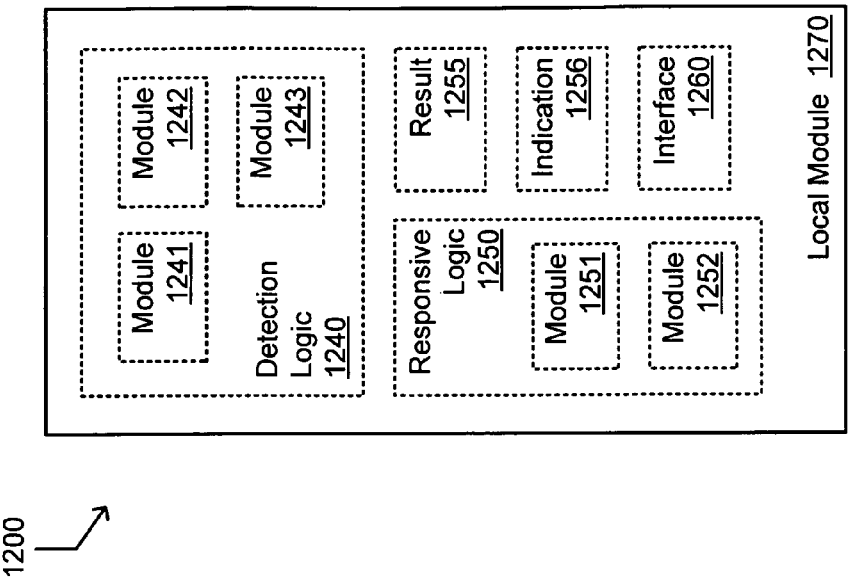

With reference now to FIG. 12, shown is a system 1200 in which one or more technologies may be implemented. One or more wearable straps or other such local modules 1270 may, for example, comprise one or more modules 1241, 1242, 1243 of detection logic 1240; modules 1251, 1252 of responsive logic 1250 or other circuitry for generating or using detection results 1255 or other indications 1256 as described below; or interfaces 1260 for interacting with a healthcare recipient or other such user.

An embodiment provides a seatbelt comprising one or modules 1242 of detection logic 1240 configured as circuitry for causing one or more evaluations of incoming signals indicating a status of an occupant's seat, back, feet, or other force-bearing body parts that may suffer poor circulation or other such localized health problems for long periods. Such embodiments may be used, for example, in a context in which an occupant is cognitively or otherwise unable to respond to such problems. In some variants, such a worn article may include or otherwise support elastic or other tensile elements configured to urge sensors toward a sitting healthcare recipient. In some embodiments, "health status" indicative data can reflect a physiological trend or other time-dependent phenomenon indicating some aspect of a healthcare recipient's condition. Alternatively or additionally, a health status indicative data set can include portions that have no bearing upon a given healthcare recipient's health. Although some types of distillations can require authority or substantial expertise (e.g. making a final decision upon a risky procedure or other course of treatment), many other types of distillations can readily be implemented without undue experimentation in light of teachings herein.

An embodiment provides a positioning structure or other local module 1270 configured to be worn by a healthcare recipient, one or more receivers or other modules 1252 of responsive logic 1250 supported by the positioning structure and configured to receive an indication 1256 of a medical procedure, regimen, or other option or intention of a caregiver (as a wireless or other signal, e.g.), and one or more interfaces 1260 or other such user interaction devices supported by the positioning structure and configured to present at least some such indications relating to health in a vicinity of the healthcare recipient. Other such embodiments are described above, for example, with reference to FIGS. 1-5.

In some variants, such detection logic may be implemented in hosiery, wristbands, bandages, or other such worn articles. Other such embodiments are described, for example, with reference to FIGS. 1-5. In some variants, such embodiments may incorporate one or more existing technologies like those of the "BT2" wristwatch design, described at www.exmocare.com and in the Information Disclosure Statement filed herewith.

Figure 13:
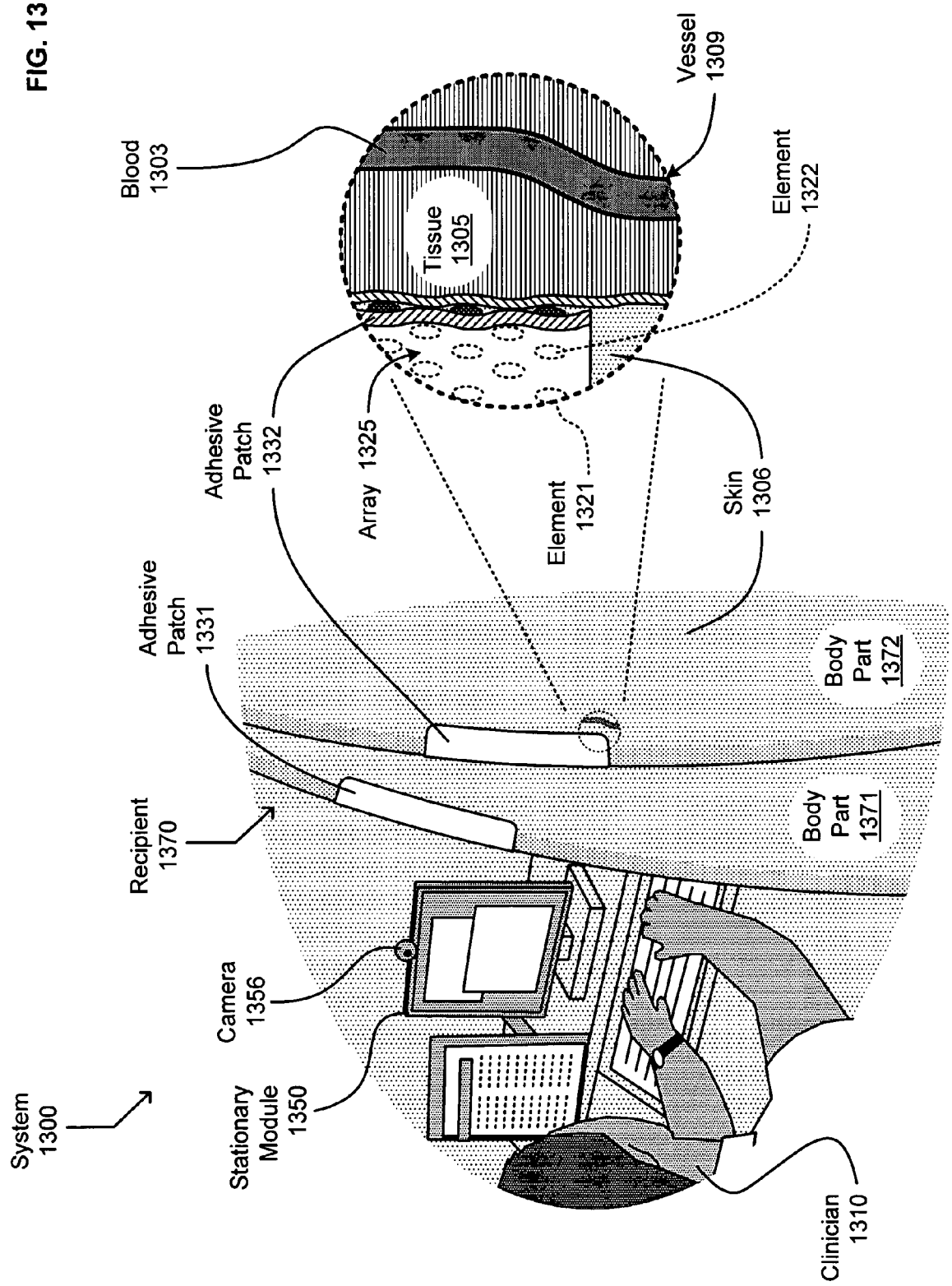

With reference now to FIG. 13, shown is a system 1300 in which one or more technologies may be implemented, such as for observing one or more attributes of body parts 1371, 1372 of healthcare recipient 1370 via one or more respective adhesive patches 1331, 1332 on the healthcare recipient's skin 1306. Adhesive patch 1332, for example, holds an array 1325 of sensor elements 1321, 1322 in close contact with skin 1306 so that attributes of subcutaneous tissues 1305, vessels 1309, or blood 1303 or other such materials may be observed. In some contexts, for example, such an array 1325 may implement combinations of two or more types of sensors and/or related logic as exemplified in relation to FIGS. 14-17 below. In some variants, for example, one or more such elements 1321, 1322 may also include a configurable colorant, a light-emitting diode, or other such external feature detectable by a clinician 1310 and/or by a stationary module 1350 or other apparatus that contains a camera 1356 or other optical sensor.

An embodiment provides one or more elements 1322 configured as circuitry for deciding whether to transmit one or more blood clot indications (detected with reference, for example, to one or more components sensed within blood 1303 by element 1321) and an adhesive patch 1332 comprising one or more tensile elements configured to hold such elements 1321, 1322 of array 1325 in tight contact with skin 1306. (Other such embodiments are described, for example, with reference to FIG. 10.) Such embodiments may be used, for example, in a context in which each contact element 1321, 1322 comprises a gel-filled capsule or otherwise includes a liquid-containing medium configured to facilitate acoustic energy passing to or from healthcare recipient 1370.

In some variants, system components described herein may be configured to include adhesive, fluid, electrically conductive, and/or other special-purpose substances facilitating effective skin contact. Alternatively or additionally, system components described herein may be configured to facilitate positioning one or more sensors in contact with or in close proximity to a healthcare recipient's skin. Alternatively or additionally, in some variants, a stationary module 1350 may include one or more cameras 656, 1356 or other components configured to obtain an image of the output device (as a wireless or other signal, e.g.).

Figure 14:
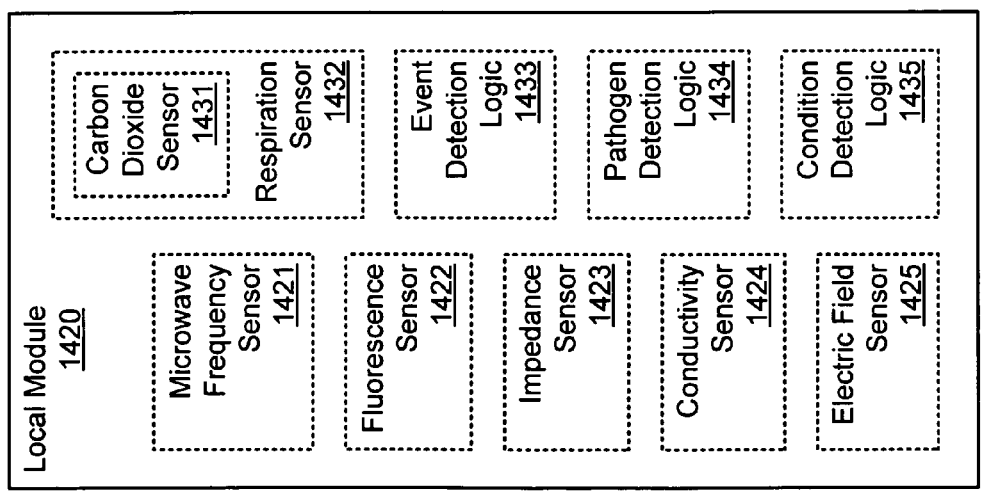

With reference now to FIG. 14, shown is a local module 1420 in which one or more sensor technologies may be implemented, such as for monitoring a device or region, or other such tasks as described herein. In some embodiments as described herein, such modules may include one or more microwave frequency sensors 1421, optionally configured to generate an indication of moisture or related symptoms in or on a healthcare recipient's body. Alternatively or additionally, local module 1420 may include one or more fluorescence sensors 1422, optionally configured to generate an indication of one or more artificial markers in or on specific tissue. (In many contexts, for example, such markers may be used for monitoring targeted physiological constituents and/or pathogens.) Such modules may likewise include one or more impedance sensors 1423, optionally configured to generate healthcare recipient respiration rate indications, to detect fractures or other changes in electrode contact surfaces or other such artificial structures, or to detect other such circumstances relating to a healthcare recipient of interest. Alternatively or additionally, local module 1420 may include one or more conductivity sensors 1424, optionally configured to monitor sweat, apparent urinary incontinence, or other such external circumstances and/or (internally) to monitor blood flow, electrolyte levels, or other such internal conditions. Such modules may likewise include one or more electric field sensors 1425 in some variants as described herein, optionally comprising (a) an implanted sensor configured to monitor nerve traffic, (b) an implanted or contact sensor configured to transmit electrocardiogram signals, brain activity indications, or other such status information about a healthcare recipient. Alternatively or additionally, local module 1420 may include one or more carbon dioxide sensors 1431 or other respiration sensors 1432, optionally comprising a sensor implanted adjacent a target site and configured to monitor one or more indications of concentration, for example, to detect apparent occlusions of a blood vessel near the site. Such modules may likewise include one or more instances of event detection logic 1433, pathogen detection logic 1434, or other condition detection logic 1435 such as for comparing raw output from sensors as described herein with prior or other sensor output, with threshold values to determine an apparent occurrence of an event, or with other condition attributes as described herein for triggering notification or therapy. In some embodiments, several or all of such items may be included in a single instance of local module 1420.

Figure 15:
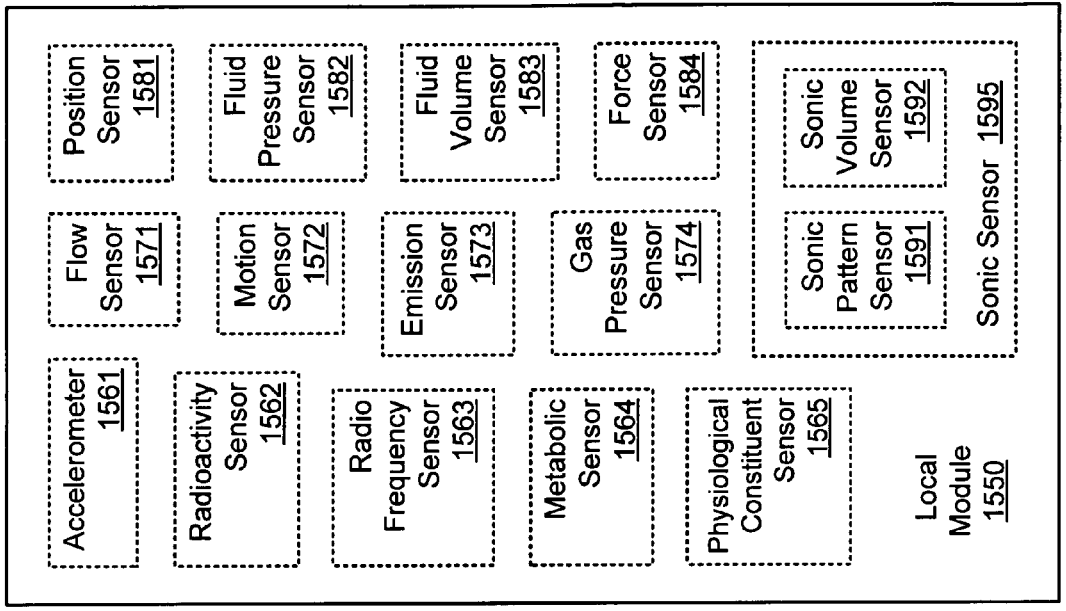

With reference now to FIG. 15, shown is a local module 1550 in which one or more sensor technologies may be implemented, such as for monitoring a device or region, or other such tasks as described herein. In some embodiments as described herein, such modules may include one or more accelerometers 1561, supported in a fixed relation to a target area, optionally configured to generate an indication of the activity, motion, and/or orientation of the healthcare recipient and/or region. Alternatively or additionally, local module 1550 may include one or more radioactivity sensors 1562, optionally configured internally or externally to generate an indication of one or more artificial markers in or on specific tissue. (In many contexts, for example, such markers may be indicative of levels of administered therapeutic components, rates of adsorption or elimination of components, exposure levels to external radioactive materials, or other pathological or other biological processes.) Such modules may likewise include one or more radio frequency sensors 1563, optionally configured to facilitate communication to, from, or between implanted or external devices, and/or to detect lung- or other such organ-status-indicative information in circumstances in which coupling via a continuous conduit may be undesirable. In some variants, local module 1550 may contain one or more metabolic sensors 1564, optionally configured as an implanted device or an external component configured to monitor the healthcare recipient or region (ex situ or otherwise) and to generate an indication of uptake, breakdown, elimination, and/or other such metabolic processes relating, for example, to therapeutic materials as described herein. In some contexts, for example, such a metabolic sensor may be configured to indicate a generation and/or elimination of other components resulting from the breakdown of therapeutic components, the use or generation of physiological constituents resulting from glucose transforming into carbon dioxide or other such metabolic processes. Such modules may likewise contain one or more physiological constituent sensors 1565, optionally comprising an implanted or other sensor configured to generate an indication of physiological constituent levels observed in a healthcare recipient or subject region. This may include items such as chemical components (e.g. calcium, sodium, cholesterol, pH), proteins and protein complexes (e.g. hemoglobin, insulin, binding proteins, antibodies) and/or structures (e.g. red and/or white blood cells, bacteria, viruses, platelets).

Alternatively or additionally, local module 1550 may likewise (optional) include one or more flow sensors 1571, which may be configured to generate an indication of fluid flow in or across a region of interest. (In many contexts, for example, such phenomena as blood flow through a vein or artery, urine flow through a urethra, bile flow through a bile duct, or other fluid flow from one region to another may be monitored.) Alternatively or additionally, local module 1550 may include one or more motion sensors 1572, optionally configured internally, externally, and/or remotely to give an indication of the motion and/or activity of a device or a portion of a healthcare recipient. Such modules may likewise include one or more emission sensors 1573, optionally configured to internally or externally give an indication of patient or region status such as using emitted infrared wavelength and intensity levels as an indication of patient or region temperature. Other emission processes may be used to monitor artificial markers in or on tissue, for example, for monitoring specific tissue features, processes, constituents, and/or pathogens. Alternatively or additionally, local module 1550 may include one or more gas pressure sensors 1574 configured to monitor ambient pressure levels, applied pressure levels (in hyperbaric chambers, continuous positive airway pressure machines, respirators, or other such artificial devices) and/or pressure levels observed in a gas-filled support structure. (In some variants, pressure may likewise be indicated by a variety of indirect measures such as blood vessel thickness, pulse energy, position, noise, or other physical phenomena correlated therewith.) Local module 1550 may likewise include one or more position sensors 1581 configured to monitor patient and/or region orientation. Alternatively or additionally, local module 1550 may include one or more fluid pressure sensors 1582, optionally configured to transmit or otherwise respond to physiological fluid pressure (aneurysm sac pressure or cranial pressure, e.g.) or external fluid pressure (as an indication of delivery amount and/or proper function in a therapeutic delivery system, for example, or in a fluid-filled support structure as described herein). Such modules may likewise contain one or more fluid volume sensors 1583, optionally configured to give an indication of fluid volumes within a patient or region such as blood volume in a heart chamber, artery, or lung (as a measure of disease progression or risk, e.g.). Alternatively or additionally, local module 1550 may include one or more force sensors 1584, optionally configured (a) to generate a pressure reading or other indication of force applied to a region (as a measure of tissue rigidity, e.g.) or (b) to indicate glaucoma, compartmental syndromes, abnormal structures, or other such potential pathologies. Such sensors may also be used as an indication of the force applied by a patient and/or region on a support structure to monitor patient activity levels and/or to give an indication of susceptibility to force/pressure related injuries such as pressure ulcers. Such modules may likewise contain one or more microphones or other sonic sensors 1595, optionally configured to enable communication to, from, and/or between implanted devices, for the recognition of sonic patterns such as heart rate, respiration rates, voice commands and other verbal input (via one or more sonic pattern sensors 1591, e.g.) or of a healthcare recipient's potential exposure to external stimuli (via one or more sonic volume sensors 1592, e.g.). In some embodiments, several or all of such items may be included in a single instance of local module 1550.

Figure 16:
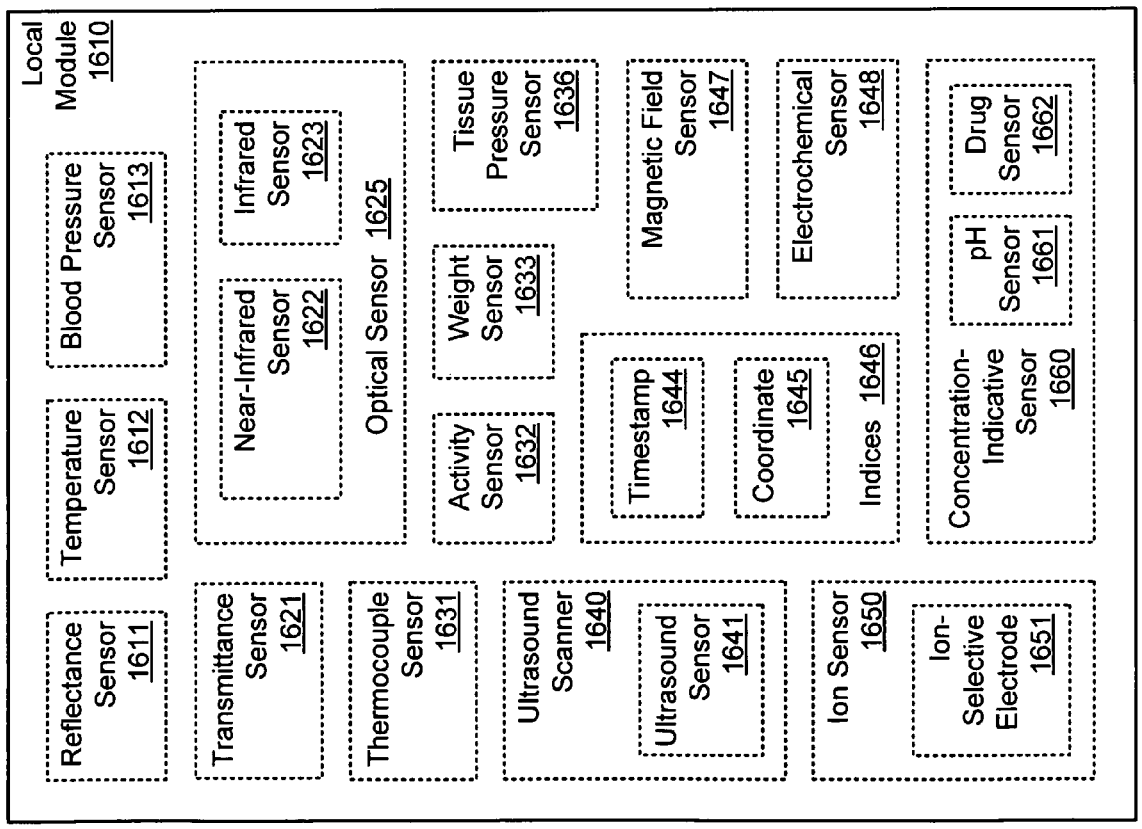

With reference now to FIG. 16, shown is a local module 1610 in which one or more sensor technologies may be implemented, such as for monitoring a device or region. In some embodiments, such modules may (optionally) include one or more temperature sensors 1612, optionally configured to give an indication of ambient thermal conditions around a patient and/or systemic or local thermal conditions of the patient. (In some embodiments, "systemic" information may refer generally to current measurements, body temperature or other such status information, or other data reflecting one or more attributes of a patient as a whole. "Local" information, by contrast, may describe measurements, images, or other such data conventionally pertaining to an identifiable portion of a patient's body.)

Such modules may be implemented using one or more thermocouple sensors 1631, for example, in implanted and/or direct contact devices. Thermal probes may likewise be implemented as optical sensors that are implanted, direct contact, and/or remotely operable. Alternatively or additionally, local module 1610 may include one or more blood pressure sensors 1613, optionally configured to give an indication of peripheral and/or systemic blood pressure of a healthcare recipient. Such modules may be configured to incorporate one or more fluid pressure sensors 1582 or conductivity sensors 1424 in some implanted contexts. Alternatively or additionally, one or more force sensors 1584 and/or ultrasound sensors 1641 (of ultrasound scanner 1640, e.g.) may be configured in a transdermal mode, for example, to generate information indicative of blood pressure. Local module 1610 may likewise include one or more near-infrared sensors 1622 and/or infrared sensors 1623 sensors, optionally configured to determine local oxygenation levels or other such chemical and/or material properties of body tissues or fluids as described herein. Such sensors can likewise be configured as transmittance sensors 1621, for example, receiving radiation that has passed through a patient fingertip or earlobe, or in other such short-path contexts such that the opacity of a tissue region allows for sufficient incident radiation to pass through it to form a usable image. Alternatively or additionally, local module 1610 may comprise one or more reflectance sensors 1611 configured to emit energy into tissue and to capture a portion of the energy reflected.

In some variants, local module 1610 may contain one or more activity sensors 1632, weight sensors 1633 and/or tissue pressure sensors 1636, optionally configured to give an indication of patient activity, motion, or other information indicative of systemic or local physical status. Such modules may likewise include one or more magnetic field sensors 1647, optionally configured to allow for the control and/or inhibition of implanted devices transdermally. Alternatively or additionally, local module 1610 may include mass-indicative or other electrochemical sensors 1648, any of which may (optionally) be configured to give an indication of physiological constituent levels such as by incorporating ion-selective electrodes 1651 (of ion sensor 1650, e.g.) or other concentration-indicative sensors 1660 for the monitoring of potassium, sodium, calcium, and/or other physiologically relevant components (at pH sensor 1661 or other concentration-indicative sensors 1660, e.g.). In some variants, electrochemical sensors 1648 can be used in a faradaic mode to monitor levels of other relevant physiological components such as blood glucose levels, neurotransmitter release, blood oxygen levels, or other useful components either in an implanted setting and/or a contact setting (in which the sensor is inserted through the skin to the detection site, for example, or the target molecules can be isolated from the healthcare recipient and detected externally. Such modules can also use one or more electrochemical sensors 1648 and/or optical sensors 1625 (including fluorescence sensors 1422, emission sensors 1573, near-infrared sensors 1622, or infrared sensors 1623) individually or in combination to provide information for the monitoring of a drug substance administered to the healthcare recipient (such as drug sensor 1662, e.g.). Local module 1610 may also implement one or more timestamps 1644, location coordinates 1645, or other such indices 1646 relating to measurements or other aspects of healthcare recipient status information. In some embodiments, several or all of such items may be included in a single instance of local module 1610.

Figure 17:
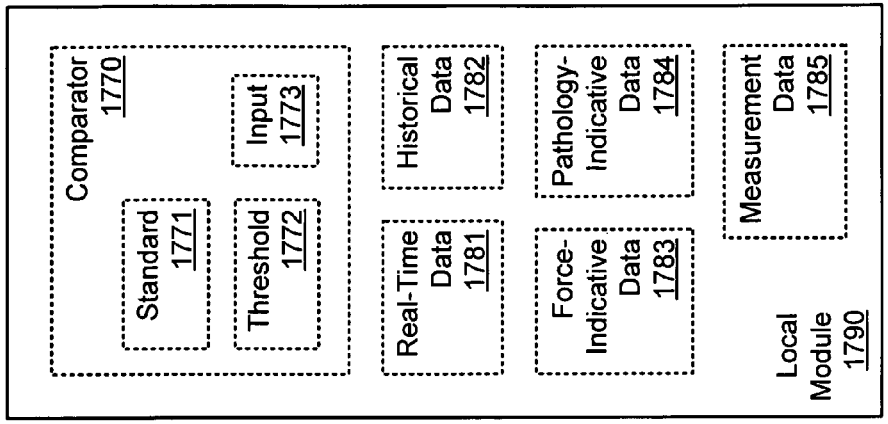

With reference now to FIG. 17, shown is a local module 1790 in which one or more technologies may be implemented, optionally within a sensor, sensor-containing module, or other local instrumentation. Any of local modules 1420, 1550, 1610 may (optionally) include one or more instances of differential or other comparators 1770 configured to process one or more instances of real-time data 1781, historical data 1782, force-indicative data 1783, pathology-indicative data 1784, measurement data 1785 using one or more standards 1771, thresholds 1772, or other input 1773. Those skilled in the art will recognize, for example, how to apply one or more thresholds 1772 configured to implement conditional retention, conditional transmission, or other such selective treatment to pressure-indicative, shear-indicative, strain-indicative, stress-indicative, deformation-indicative, acceleration-indicative, or other such force-indicative data 1783 in light of teachings herein.

An embodiment provides an adhesive patch 1332 or other positioning structure 760 configured to be worn by a healthcare recipient 1370, 2010; one or more receiver and/or display elements 1321 supported by the positioning structure and configured to receive a signal 682; and one or more receiver and/or display elements 1322 supported by the positioning structure and configured to present or otherwise transmit an alert or other health-related information 740 responsive to signal 682 and to one or more status updates relating to the healthcare recipient. This can occur, for example, in a context in which such status updates 735 include physiological parameters 635, images, or other such indications from sensors on or inside the recipient. Alternatively or additionally, article 610 may include or communicate with one or more implants or adhesive patches 1331, 1332 implementing one or more local modules 1420, 1550, 1610, 1790 operable to detect physiological phenomena of interest. In some variants, for example, condition detection logic 1435 may be configured to detect real-time data 1781 indicating that a healthcare recipient 950 is apparently not exhibiting high enough and/or steady enough concentrations of a nutrient or medication, or other such phenomena. Other such embodiments are described above, for example, with reference to FIGS. 1-9.

Figure 18:
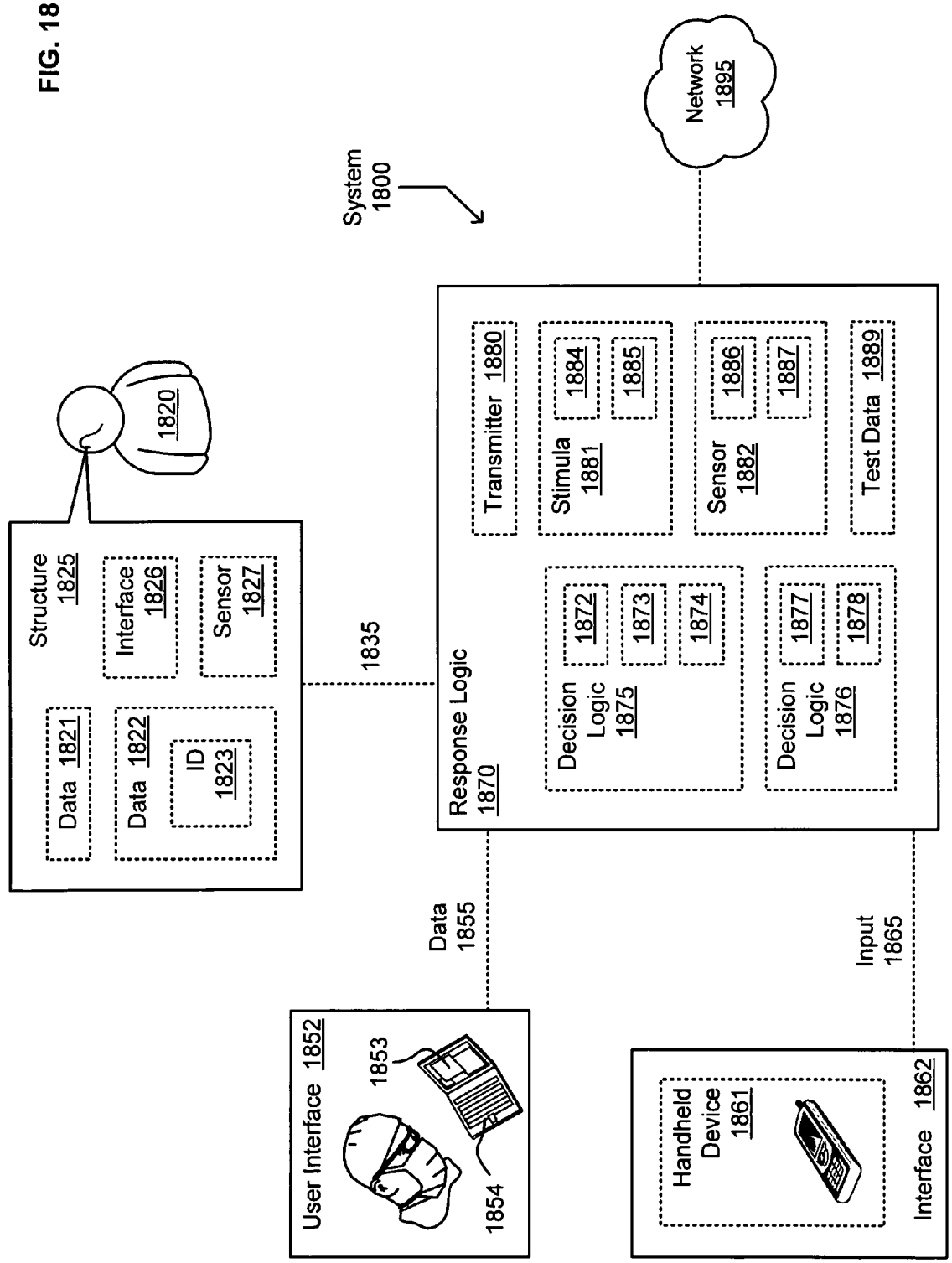

With reference now to FIG. 18, shown is an example of a system 1800 that may serve as a context for introducing one or more processes and/or devices described herein, optionally configured to interact with network 1895. As shown system includes one or more modules 1872, 1873, 1874, 1877, 1878 of decision logic 1875, 1876; one or more transmitters 1880; and/or one or more parameters 1884, 1885 of stimula 1881 selected to facilitate one or more sensors 1882 obtaining sensed values 1886, 1887 or other such test data 1889 about an individual or subpopulation to be monitored. System 1800 may also include or otherwise interact with one or more instances of structures 1825 configured to obtain data from healthcare recipients 1820, user interfaces 1852 configured to interact with decision makers or expert resources, or handheld devices 1861 or other such interfaces 1862 for relaying input 1865 to or from other such parties.

Headgear or other structures 1825 wearable by healthcare recipient 1820 may include, for example, one or more instances of identifiers 1823, status updates, or other data 1821, 1822 about healthcare recipient 1820 obtained via one or more interfaces 1826 and/or sensors 1827. User interface 1852 may likewise present visual or other output 1853 and/or receive keyed or other input 1854. Response logic 1870 as an entity may receive and/or transmit a variety of interactive data 1855 or other signals 1835 for or from network 1895, in some contexts, as exemplified below. In various examples below, for example, one or more such patients, caregivers, or others are potential message or other notification recipients. Some such entities have a priori information associating a recipient identifier or other indicator with current signals 1835 or other data as described below.

Some variants include one or more modules 1872 of decision logic 1875 comprising circuitry for transmitting a common graphical image containing information indicating a current local stress in a peripheral part of the healthcare recipient's body with information indicating a prior local stress in the peripheral part of the healthcare recipient's body. This can occur, for example, in a context in which module 1872 invokes transmitter 1880 to cause one or more composite images or other such successive indications relating to a subject's limb or back to output 1853. This can occur, for example, in a context in which a local system or mediation module 1910 uploads such images or other measurement data to an implementation of response logic 1870 in network 1990, for example, responsive to a request that remote users may generate after notifications as described herein. Alternatively or additionally, one or more such users may respond by modifying one or more standards 1771 or configurations of buffers, in some variants, so that subsequent sense data may result in other patterns of data capture and/or notification as described herein.

In light of teachings herein, numerous existing techniques may be applied for the transmission of graphical images of subject body parts for display and storage as described herein without undue experimentation. See, e.g., U.S. Pat. No. 7,310,564 ("Arrangement and method for producing therapeutic insoles"); U.S. Pat. No. 7,289,883 ("Apparatus and method for patient rounding with a remote controlled robot"); U.S. Pat. No. 7,286,877 ("Device programmer with enclosed imaging capability"); U.S. Pat. No. 7,158,861 ("Tele-robotic system used to provide remote consultation services"); U.S. Pat. No. 7,016,467 ("Mobile digital radiography x-ray apparatus and system"); U.S. Pat. No. 6,625,252 ("Emergency vehicle with medical image scanner and teleradiology system"); U.S. Pat. No. 6,621,918 ("Teleradiology systems for rendering and visualizing remotely-located volume data sets"); U.S. Pat. No. 6,612,982 ("Fully-swallowable endoscopic system"); U.S. Pat. No. 6,529,757 ("Picture archiving and communication system and method for multi-level image data processing"); U.S. Pat. No. 6,490,490 ("Remote operation support system and method"); U.S. Pat. No. 6,137,527 ("System and method for prompt-radiology image screening service via satellite").

Some variants include one or more modules 1873 of decision logic 1875 comprising circuitry for relating local circulatory information to one or more of a thigh location, a calf location, or a foot location of a leg of the healthcare recipient. This can occur, for example, in a context in which module 1873 of decision logic 1875 receives signal 1835 or other data causing an activation of one or more sensors identified with or otherwise identifying such a body portion within recipient 1820. This can occur, for example, in a context in which one or more sensors 1827 are positioned on or near the subject portion). In some contexts, for example, one or more such portions may be selected as a primary sensor location for (local) body part monitoring. Alternatively or additionally, one or more other sensors as described with reference to FIG.

14-17 may be positioned to monitor such subject portions and/or other contemporaneous attributes of the healthcare recipient as described herein.

In light of teachings herein, numerous existing techniques may be applied for the selective inclusion and/or activation of one or more sensors from a sensor set as a primary sensor location without undue experimentation. See, e.g., U.S. Pat. No. 7,332,743 ("Thin film transistor array panel and liquid crystal display"); U.S. Pat. No. 7,208,983 ("Image-sensor signal processing circuit"); U.S. Pat. No. 7,190,987 ("Neonatal bootie wrap"); U.S. Pat. No. 7,155,281 ("Complimentary activity sensor network for disease monitoring and therapy modulation in an implantable device"); U.S. Pat. No. 7,149,645 ("Method and apparatus for accurate on-die temperature measurement"); U.S. Pat. No. 6,275,733 ("Dual sensor rate response pacemaker"); U.S. Pat. No. 6,271,766 ("Distributed selectable latent fiber optic sensors").

Some variants include one or more modules 1877 of decision logic 1876 comprising circuitry for detecting one or more indications of normalcy as a current (thermal, inflammatory, auditory, and/or other physiological) condition in a peripheral part of the healthcare recipient. This can occur, for example, in a context in which module 1877 indicates normalcy in response to receiving a high-enough and/or low-enough numerical value 1887 directly or indirectly from one or more sensors 1827 operable for detecting a temperature at an extremity of recipient 1820. This can occur, for example, in a context in which recipient 1820 wears or otherwise interacts with structure 1825, in which decision logic 1876 is capable of detecting and indicating whether value 1887 is too far from a normal and/or uniform condition, and in which the output device(s) comprise transmitter 1880. In some variants, for example, module 1877 may employ this information as a factor in deciding whether to transmit a notification to user interface 1852 or to other destinations. Alternatively or additionally, in various implementations as described herein, structure 1825 may include one or more instances of response logic or other circuitry operable for responding conditionally to an identifier 1823 of a subject or other determinants in detected data 1822.

In light of teachings herein, numerous existing techniques may be applied for detecting statistical, anatomical, or other potentially useful aberrations in light of other circumstances as described herein without undue experimentation. See, e.g., U.S. Pat. No. 7,340,293 ("Methods and apparatus for a remote noninvasive technique to detect core body temperature in a subject via thermal imaging"); U.S. Pat. No. 7,226,426 ("Apparatus and method for the detection and quantification of joint and tissue inflammation"); U.S. Pat. No. 6,963,772 ("User-retainable temperature and impedance monitoring methods and devices"); U.S. Pat. No. 6,757,412 ("System and method for helping to determine the condition of tissue"); U.S. Pat. No. 6,126,614 ("Apparatus and method for analysis of ear, pathologies by detecting fluid in the ear measuring body temperature and/or determining a characteristic of a fluid"); U.S. Pat. No. 6,023,637 ("Method and apparatus for thermal radiation imaging"); U.S. Pat. No. 5,999,842 ("Functional thermal imaging apparatus"); U.S. Pat. No. 5,997,472 ("Endodiagnostic method using differential thermal relaxation and IR imaging").

An embodiment provides headset or other positioning structure 1825 configured to be worn by a healthcare recipient 1820, one or more interfaces 1826 or other receivers supported by the positioning structure 1825 and configured to receive a wireless or other signal 1835, and at least one speaker or other output device supported by the positioning structure 1825 and configured to present or otherwise transmit at least a pharmaceutical or other health-related identifier 1823, a response to a recipient query, or other such health-related or other data 1822 needed by recipient 1820, provided in the signal 1835, and/or responsive to data 1821 from one or more sensors 1827 in proximity to the recipient 1820. Other such embodiments are described above, for example, with reference to FIGS. 1-9.

Figure 19:
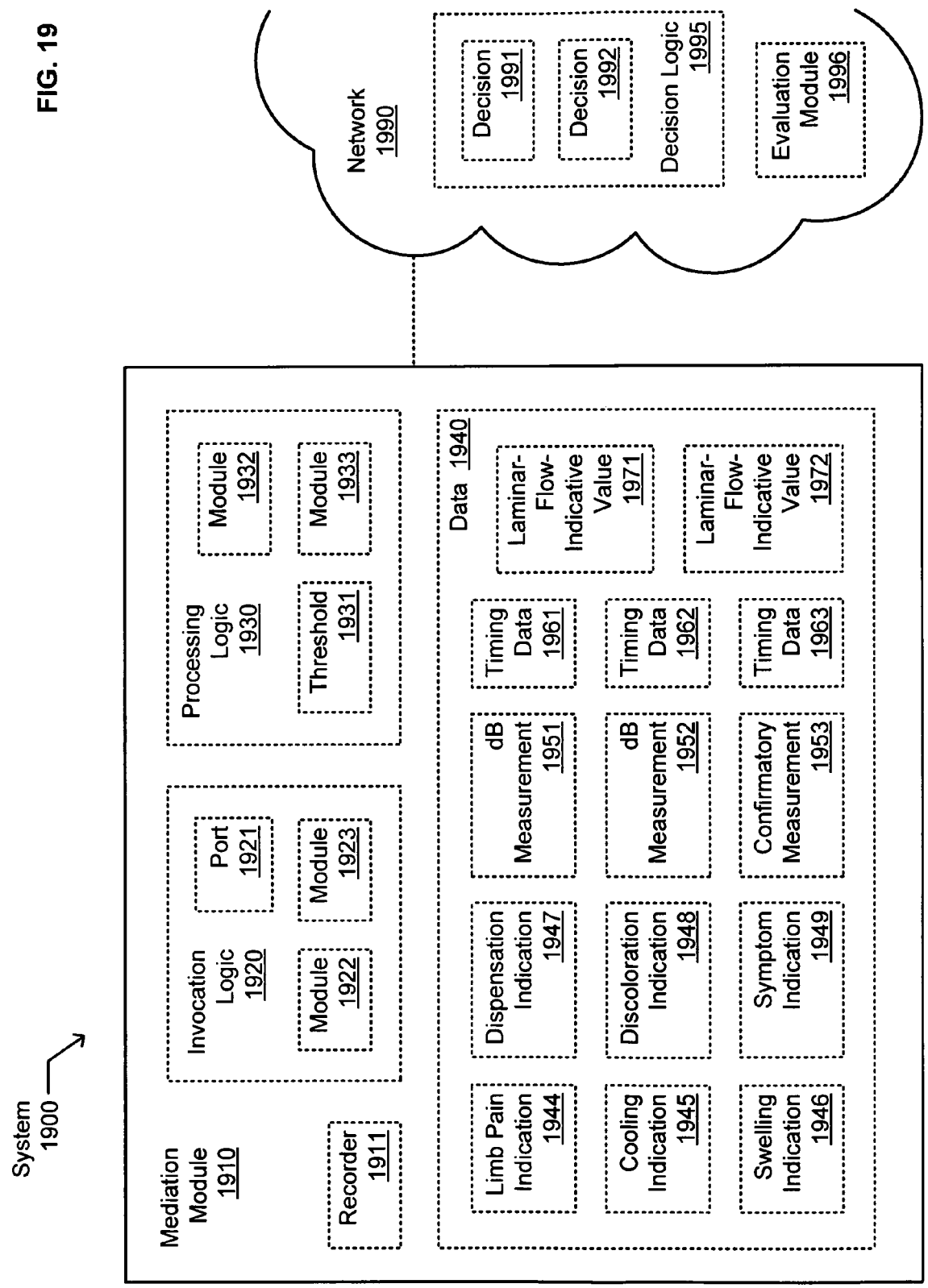

With reference now to FIG. 19, shown is a system 1900 comprising a mediation module 1910, such as may be configured to facilitate data aggregation or other such data-transformative interaction between one or more networks 1990 and a primary or other local system as described herein. Mediation module 1910 may include one or more recorders 1911; ports 1921, modules 1922, 1923 or other invocation logic 1920; or modules 1932, 1933 or other processing logic 1930, such as for applying a threshold 1931. Such components may, for example, trigger a recording or analysis in response to one or more instances of limb pain indications 1944, cooling indication 1945, swelling indications 1946, dispensation indications 1947, discoloration indications 1948, symptom indications 1949, decibel measurements 1951, 1952, timing data 1961, 1962, 1963, or a low-enough Reynolds number computation or other laminar-flow-indicative value 1971, 1972. In some variants, moreover, these or other data types may be used as confirmatory measurements 1953 or other data configured for a contingent confirmation of a follow-up evaluation, a diagnosis, a referral, a prognosis, or some other hypothesis of potential therapeutic relevance. In some variants, for example, invocation logic 1920 may trigger one or more decisions 1991, 1992 or other responses from decision logic 1995, a remote evaluation module 1996, or other such entities. Alternatively or additionally, some or all such data 1940 may be transmitted to network 1990, for example, to permit such recording or other functions to be performed remotely.

Some variants include one or more modules 1932 of processing logic 1930 comprising (software-implemented or other) circuitry for obtaining a turbulence-indicative auditory value as a flow-change-indicative measurement. This can occur, for example, in a context in which module 1932 accepts one or more (past or present) decibel measurements 1951, 1952 high enough to indicate turbulence in a blood vessel. This can occur, for example, in a context in which module 1933 associates an earlier laminar-flow-indicative value 1971 or a later laminar-flow-indicative value 1972 (a Reynolds number or other such measurement below a turbulence-indicative threshold 1931, e.g.) with timing data 1961 signifying an appearance or disappearance of detectable turbulence in the blood vessel. In some variants, for example, such transition-indicative timing data may signify a growing thrombosis, a thrombosis breakage, a therapeutic success, or other such flow-change-indicative phenomena. Alternatively or additionally, invocation logic 1920 may trigger one or more remote evaluation modules 1996 to evaluate whether such timing data sufficiently coincides with timing data 1962 of a dispensation, timing data 1963 of a pressure-indicative or other confirmatory measurement 1953, or other such therapeutically relevant and detectable events.

Some variants include one or more modules 1922 of invocation logic 1920 comprising circuitry for signaling at least a clot-reducing agent in response to an apparent circulatory degradation. This can occur, for example, in a context in which module 1922 receives and relays the decision 1991 to administer one or more therapeutic components to a nurse or other party cable of administering such agents via port 1921. This can occur, for example, in a context in which mediation module 1910 interacts with a local module as described herein via port 1921 and in which such flow degradation manifests as one or more of a complaint or other severe limb pain indication 1944, a swelling indication 1946, a local discoloration indication 1948, other such detectable phenomena local to a portion of healthcare recipient's body, or as a confirmatory measurement 1953 (in combination with such indications, e.g.). In some variants, moreover, another module 1923 may signal a caregiver to check one or more potential effects of the clot-reducing or other therapeutic agents or to provide other appropriate follow-up. Alternatively or additionally, module 1922 may invoke recorder 1911 to capture a distillation of one or more dispensation indications 1947, symptom indications 1949, and/or related timing data 1963 selectively for future evaluation.

In some variants, the one or more positioning modules may be configured to receive health-related or other information via a stationary or other mediation module 1910, for example, in a healthcare facility 405. Such information may include limb pain indications 1944, swelling indications 1946, confirmatory measurements 1953, timing data 1961, circulatory data, decisions 1991, or other such data 1940. In some contexts, for example, one or more stationary modules 810, physicians 821 or other parties 822, decision logic 1995, or other such resources 850 (in a remote or other network 1990, e.g.) may provide or respond to such symptom indications 1949 or other health indicia. Other such embodiments are described above, for example, with reference to FIGS. 1-9.

Figure 20:
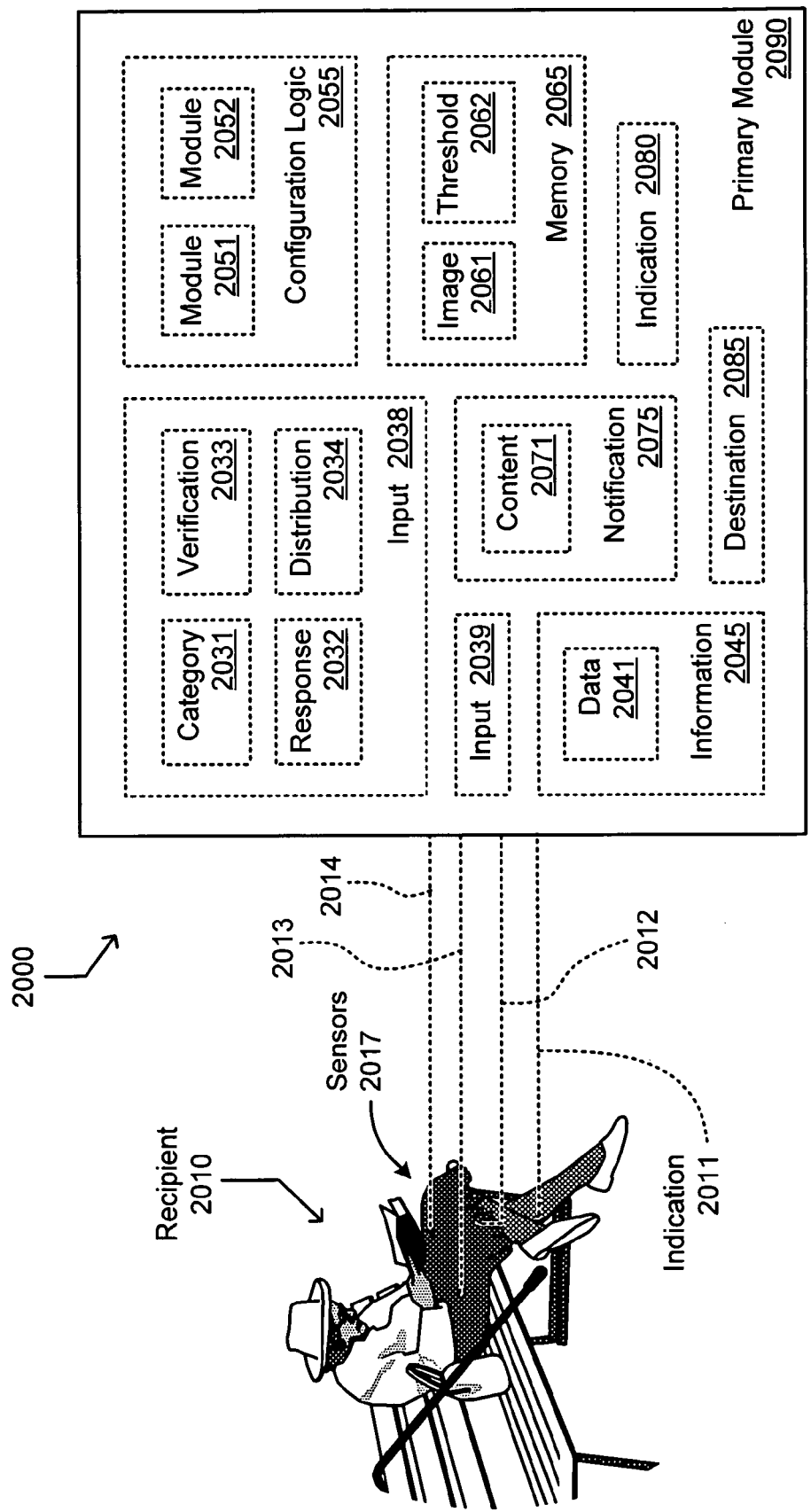

With reference now to FIG. 20, shown is a system 2000 comprising a primary module 2090 configured to accept indications 2011, 2012, 2013, 2014 from one or more auditory or other sensors 2017 in, on or about a healthcare recipient 2010. In some variants, inputs 2038, 2039 or other information 2045 as described herein may include one or more categories 2031, responses 2032, verifications 2033, distributions 2034, or other such data 2041 suitable for inclusion, for example, as content 2071 of a notification 2075. Alternatively or additionally, one or more modules 2051, 2052 or other configuration logic 2055 may maintain one or more images 2061, apply one or more thresholds 2062, or otherwise provide one or more indications 2080 or notification destinations 2085 in response to then-current contents of memory 2065.

In some embodiments, data can be "acceptable" to a data analysis module if some or all of the data can be processed by the module with success. An indication of acceptable data can be appropriate in response to detecting an apparent presence or absence of a pattern in the data, for example, or to determining that the data has a file size or header format that is typical for data processed by the analysis module.

Some variants include one or more modules 2052 of configuration logic 2055 comprising (software-implemented or other) circuitry for including at least some medical history data in the health-related information. This can occur, for example, in a context in which module 2052 includes a category 2031, response 2032, verification 2033, distribution 2034, or other caregiver input 2038 within or otherwise with notification content 2071. This can occur, for example, in a context in which various healthcare recipients 2010, caregivers, or other parties provide such input as described herein and in which these or other inputs 2038, 2039 may affect what the notification includes and/or whether or where the notification is transmitted. In some variants, for example, module 2052 may respond to an indication 2080 of a resource availability change, such as by rerouting, rescheduling, or otherwise reconfiguring a potential or partial notification's content or delivery parameters. Alternatively or additionally, an indication of a lack of timely input (from a first caregiver, e.g.) may be included in a notification to another caregiver, in some variants.

In light of teachings herein, numerous existing techniques may be applied for configuring a notification to include or otherwise indicate user preferences, status, or other such input as described herein without undue experimentation. See, e.g., U.S. Pat. No. 7,325,054 ("System for notifying destination user when status of consumable products of printing devices meets user selected notification condition"); U.S. Pat. No. 7,209,955 ("Notification system and method for a mobile data communication device"); U.S. Pat. No. 6,968,294 ("Automatic system for monitoring person requiring care and his/her caretaker"); U.S. Pat. No. 6,907,375 ("Method and apparatus for dynamic checking and reporting system health"); U.S. Pat. No. 6,878,111 ("System for measuring subjective well being"); U.S. Pat. No. 6,277,071 ("Chronic disease monitor"); U.S. Pat. No. 6,190,313 ("Interactive health care system and method").

Some variants include one or more modules 2051 of configuration logic 2055 comprising circuitry for performing a comparison using an updated normalcy threshold. This can occur, for example, in a context in which module 2051 changes or otherwise updates one or more optical or other normalcy thresholds 2062. This can occur, for example, in a context in which such comparative information is derived from sensor data described herein, and in which one or more users or devices have indicated an availability to receive such notifications with one or more such parametric updates. In some variants, for example, information from one or more sensors 2017 on or near a healthcare recipient 2010 may be used to generate and/or adjust thresholds applied to sensor data 2041 from one or more other sensors extending into, in contact with, or otherwise arranged around the healthcare recipient. Alternatively or additionally, historic and/or processed information from a remote storage and/or processing device may be used to provide and/or adjust thresholds or other filtering information applied to the sensor data 2041 or other types of information 2045 obtained about the subject limb.

In light of teachings herein, numerous existing techniques may be applied for requesting, receiving, or otherwise interacting with numerical thresholds as described herein without undue experimentation. See, e.g., U.S. Pat. No. 7,250,855 ("False alarm mitigation using a sensor network"); U.S. Pat. No. 7,079,035 ("Method and apparatus for controlling an alarm while monitoring"); U.S. Pat. No. 7,037,273 ("Core body temperature monitoring in heart failure patients"); U.S. Pat. No. 6,942,626 ("Apparatus and method for identifying sleep disordered breathing"); U.S. Pat. No. 6,569,095 ("Adaptive selection of a warning limit in patient monitoring"); U.S. Pat. No. 6,552,531 ("Method and circuit for processing signals for a motion sensor"); U.S. Pat. No. 6,263,243 ("Rate adaptive pacemaker").

Figure 21:
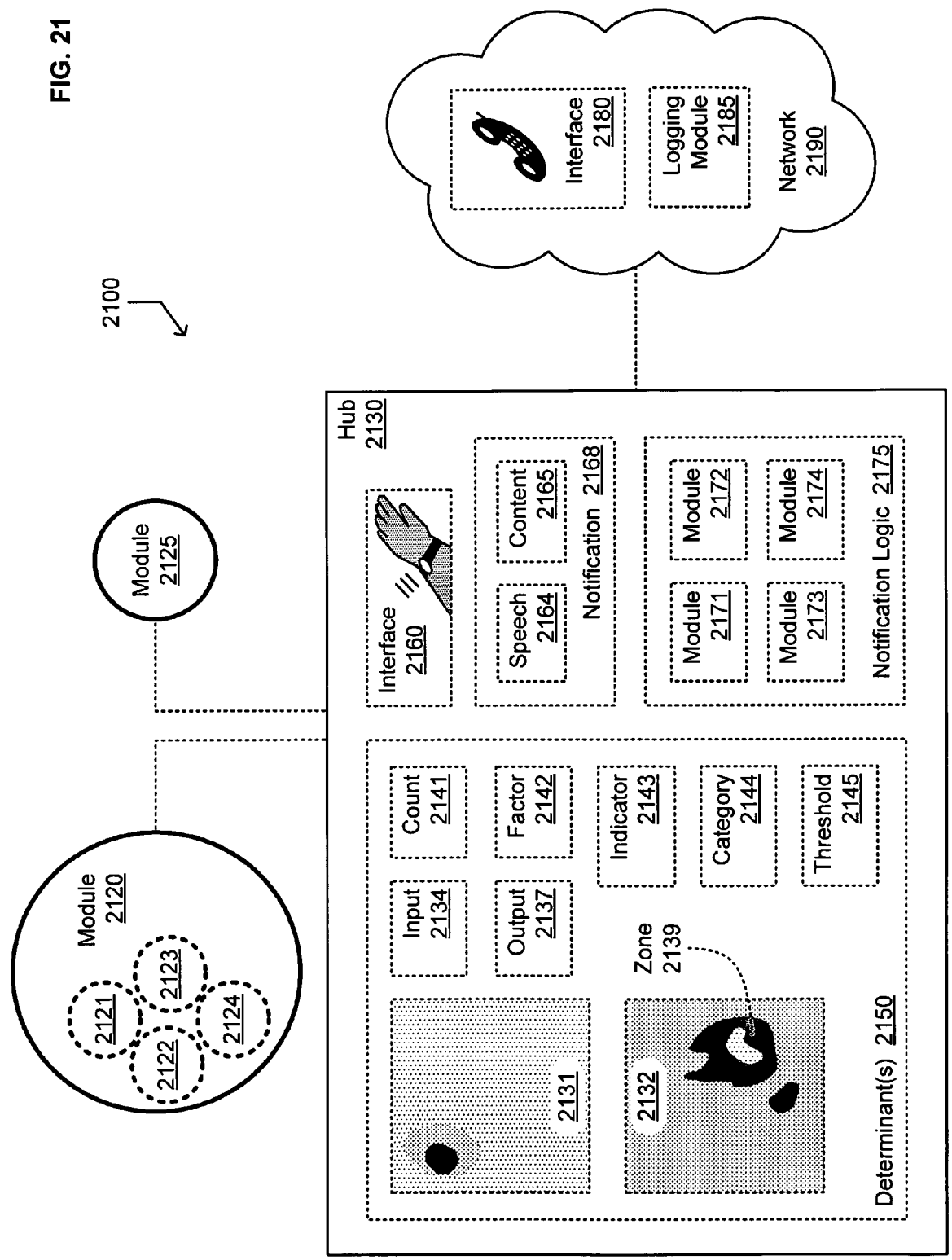

With reference now to FIG. 21, shown is a system 2100 comprising one or more modules 2120, 2125 in communication with a hub 2130 having access to one or more networks 2190. In some variants, for example, a module 2120 worn by a healthcare recipient may include one or more receivers 2121 and/or user interaction devices 2122, one or more sensors 2123, 2124 operable for transmitting one or more images 2131, 2132 (depicting zone 2139, e.g.), counts 2141, outputs 2137 from sensors, indicators 2143, thresholds 2145 or other factors 2142 to be applied, or other such determinants 2150. Alternatively or additionally, hub 2130 may receive (via one or more interfaces 2160, e.g.) one or more categories 2144 or other such input 2134 from a user or other local entity. In response to such determinants, one or more modules 2171, 2172, 2173, 2174 of notification logic 2175 may configure one or more notifications 2168 for local delivery (via interface 2160, e.g.) and/or delivery to one or more interfaces 2180 or logging modules 2185 of network 2190. In some contexts, module 2172 may configure notification 2168 to include a raw sample of slurred speech 2164 provided by a healthcare recipient in response to programmatic queries, for example, or other such content 2165 of an established diagnostic regimen. Such content may be omitted, in some contexts, in response to a determination that such content is normal (not slurred, e.g.) as described herein.

An embodiment provides a sensing unit 952, interface unit 953, 954, module 2120, or other such positioning structure, one or more receivers 2121, supported by the positioning structure and configured to receive a wireless or other signal (from hub 2130, e.g.), and one or more user interaction devices 2122 supported by the positioning structure and configured to present at least some health-related content 2165 or other notifications 2168 in a vicinity 955 of the healthcare recipient 950 responsive to signal. Other such embodiments are described above, for example, with reference to FIGS. 1-9.

Figure 22:
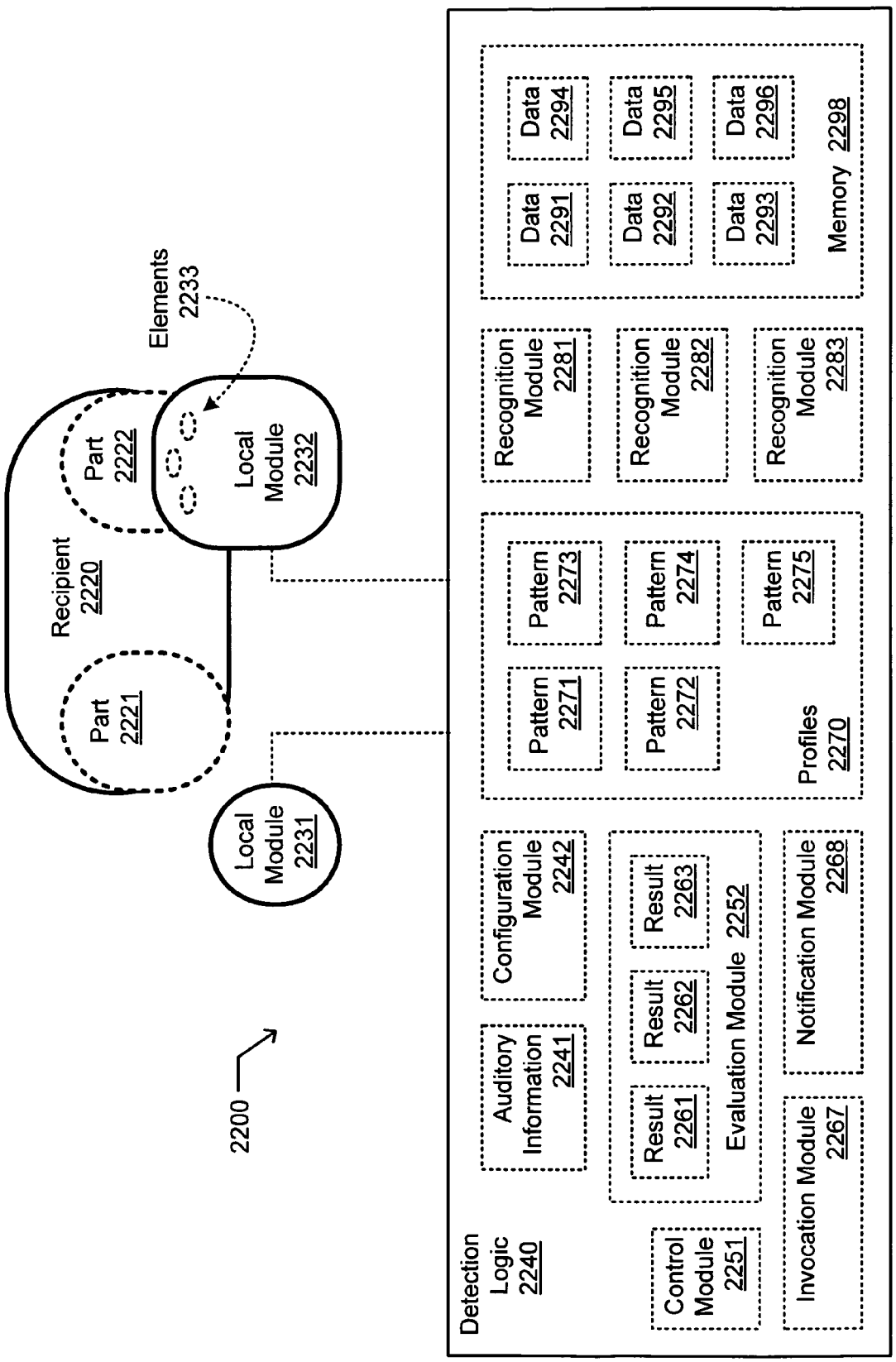

With reference now to FIG. 22, shown is a system 2200 comprising one or more local modules 2231, 2232 each in a vicinity of one or more body parts 2221, 2222 of healthcare recipient 2220. In some contexts, such local modules 2232 may include one or more sensors, support elements, dispensers, or other such elements 2233 positioned in contact with or otherwise adjacent a body part 2222 of interest. In various applications, detection logic 1240, 2240 may include one or more instances of configuration modules 2242, control modules 2251, invocation modules 2267, notification modules 2268, or various recognition modules 2281, 2282, 2283 configured to process auditory information 2241 or other input data as described herein. Such detection logic may (optionally) include one or more evaluation modules 2252 configured to implement one or more computed results 2261, comparison results 2262, user selections, or other such evaluation results 2263. Such results may arise from a recognition of one or more patterns 2271, 2272, 2273, 2274, 2275 or profiles 2270 (combinations of patterns, e.g.) evident in data 2291, 2292, 2293, 2294, 2295, 2296 residing in memory 2298. In some variants, for example, recognition module 2281 may be configured to recognize one or more extended measurement trends or other such pathological patterns 2271 even in data 2293 still in a normal range, in some contexts. Alternatively or additionally, one or more recognition modules 2282 may be configured to detect a shape, color, or other optical pattern 2275 characteristic of a scar, birthmark, or other common and/or unchanging irregularity manifested in data 2296 and not indicative of a circulatory pathology.

In some variants, such notification logic may be configured to facilitate selective notifications according to one or more controllable parameters. Other such embodiments are described, for example, with reference to FIGS. 20-23. Alternatively or additionally, one or more recognition modules 2281 may be configured to recognize one or more extended measurement trends or other such pathological patterns 2271 even in data 2293 still in a normal range, in some contexts. Alternatively or additionally, one or more recognition modules 2282 may be configured to detect a shape, color, or other optical pattern 2275 characteristic of a scar, birthmark, or other common and/or unchanging irregularity manifested in data 2296 and not indicative of a recognized pathology. Other such embodiments are described above, for example, with reference to FIGS. 1-9.

Some variants include one or more modules 1242 of detection logic 1240 comprise circuitry for signaling a decision whether to transmit a component of the health-related information partly in response to auditory information from a vicinity of the healthcare recipient. This can occur, for example, in a context in which module 1242 presents or otherwise transmits a notification partly in response to recognition module 2281 indicating one or more comparison results 2262 and partly in response to recognition module 2283 indicating a recognition of one or more phrases or other patterns 2273, 2274 in speech or other auditory information 2241 from healthcare recipient 2220. This can occur, for example, in a context in which such auditory information 2241 indicates that healthcare recipient 2220 may currently be impaired and in which at least one such result 2262 of comparing abnormal-temperature-indicative data 2291 with historical or other filtering data indicates that a hot zone of peripheral body part 2222 has become measurably hotter and that peripheral body part 2221 has apparently remained in a normal condition. In some contexts, for example, such normality may be inferred from abnormal-temperature-indicative data 2291 not referring to part 2221 and/or not coming from one or more local modules 2231 in a vicinity of part 2221. Alternatively or additionally, the decision may depend upon one or more other determinants such as (a) whether a current notification 1142 differs from a prior notification 1141; (b) whether interface 1180 indicates that one or more recipients are apparently online; (c) whether any new comparison result reflects a new, unrecognized, and/or other urgent situation; or other criteria as described herein.

In light of teachings herein, numerous existing techniques may be applied for recognizing words or other auditory patterns as described herein without undue experimentation. See, e.g., U.S. Pat. No. 7,257,531 ("Speech to text system using controlled vocabulary indices"); U.S. Pat. No. 6,990,455 ("Command and control using speech recognition for dental computer connected devices"); U.S. Pat. No. 6,934,579 ("Anaesthesia control system"); U.S. Pat. No. 6,804,654 ("System and method for providing prescription services using voice recognition"); U.S. Pat. No. 6,785,358 ("Voice activated diagnostic imaging control user interface"); U.S. Pat. No. 6,629,937 ("System for processing audio, video and other data for medical diagnosis and other applications"); U.S. Pat. No. 5,335,313 ("Voice-actuated, speaker-dependent control system for hospital bed"); U.S. Pat. No. 5,262,669 ("Semiconductor rectifier having high breakdown voltage and high speed operation").

Figure 23:
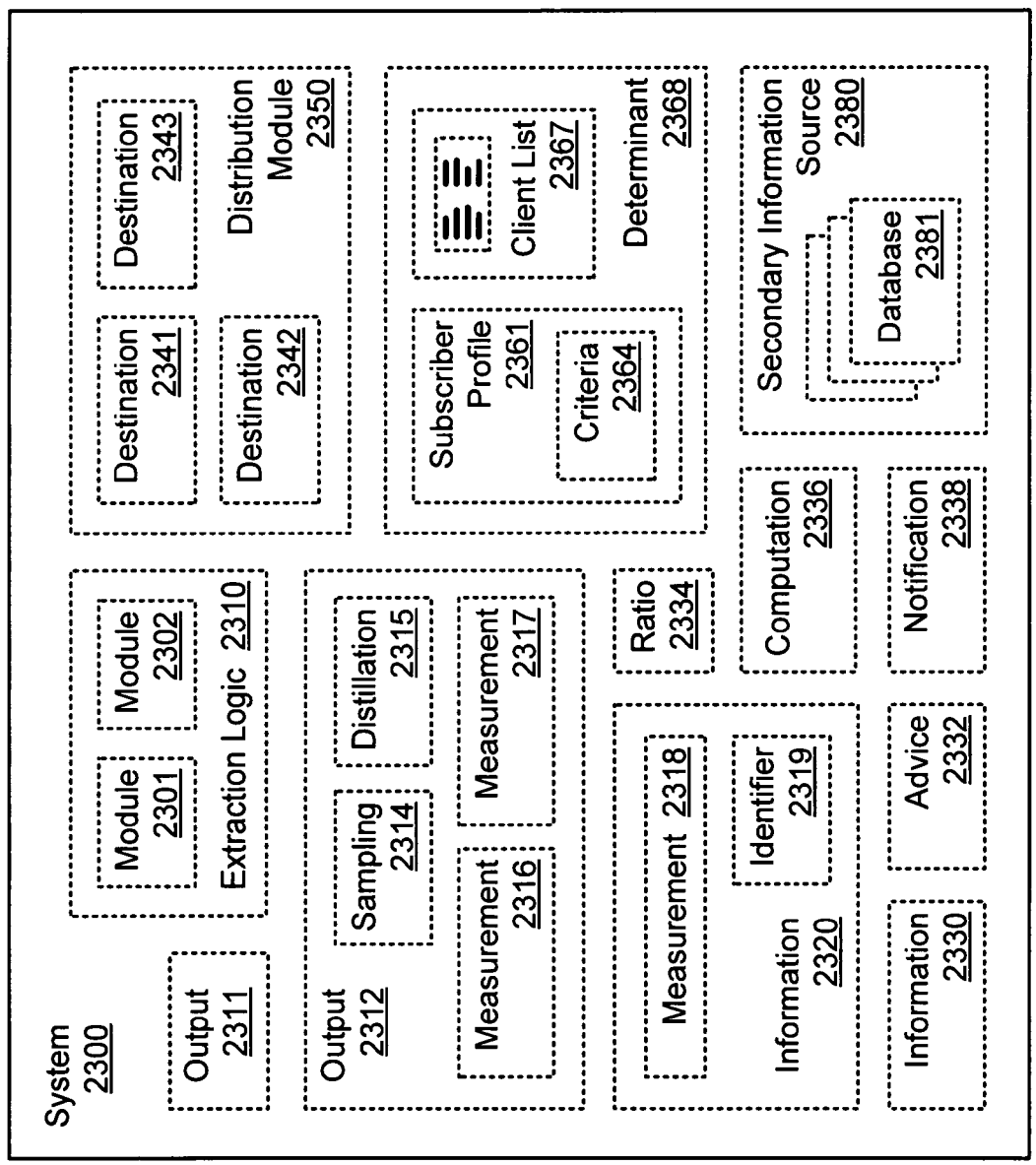

With reference now to FIG. 23, shown is a system 2300 comprising one or more modules 2301, 2302 of extraction logic 2310 configured to process one or more samplings 2314, distillations 2315, measurements 2316, 2317, 2318, identifiers 2319, or other such output 2311, 2312 from sensors or other detection logic described herein. In some embodiments, such a "distillation" can comprise an average, estimate, range, or other computation at least partly distilling a set of data. It can likewise include an indexing, sorting, summarization, distributed sampling, or other process having a purpose or effect of showing some aspect of the data more concisely or effectively than a conventional display of the entire data. Selecting a last portion of a data set can constitute a distillation, for example, in a context in which the data's utility apparently increases. Those skilled in the art will recognize many useful modes of distilling data in light of the state of the art and of teachings herein.

Such information 2320, 2330 may further include one or more instances of programmatic advice 2332, ratios 2334, computations 2336, or other such components of notifications 2338. In some variants, for example, at least one distribution module 2350 may be configured to use such information to select one or more destinations 2341, 2342 among a plurality of destinations 2341, 2342, 2343 in response to these or other criteria 2364 (defined in one or more subscriber profiles 2361, e.g.) or to a client list 2367. Alternatively or additionally, notification logic 2175 or other responsive logic described herein may use one or more such determinants 2368 to select among one or more databases 2381 or other secondary information sources 2380 to draw upon for contextual information to be included in such notifications.

In some variants, logic for applying one or more thresholds or other such criteria may be configured to preserve relevant data selectively, to generate a summary or evaluation, or otherwise to perform suitable data extractions. In some embodiments, such data extraction criteria can include maxima or other comparison values applied to durations, counts, lengths, widths, frequencies, signal magnitudes or phases, digital values or the like. Such criteria can be applied by determining when or how often a definable pattern can be found: a text string, a quantity, a cough-like sound, an arrhythmia, a visible dilation, a failure to respond, a non-change, an allergic response, a symptom relating to an apparent condition of the user, or the like.

In some contexts, a programmer or record manager may configure one or more modules 2301 of extraction logic 2310 or other response logic 335 to transmit one or more such notifications 315 to healthcare recipients, care providers, and/or other interested parties 822. Such configurations may include encoding one or more client lists 2367 and/or criteria 2364 of each subscriber profile 2361, for example, or other such determinants 2368.

In some variants, one or more such output devices may selectively present the health-related information 2320 with one or more computations 2336 of estimated cost, with updates relating to the recipient's vocations or hobbies, and/or with one or more notifications 2338 apparently unrelated to health. In some contexts, for example, such notifications may be archived and potentially correlated with physiological abnormalities that follow. Other such embodiments are described above, for example, with reference to FIGS. 1-9.

Figure 24:
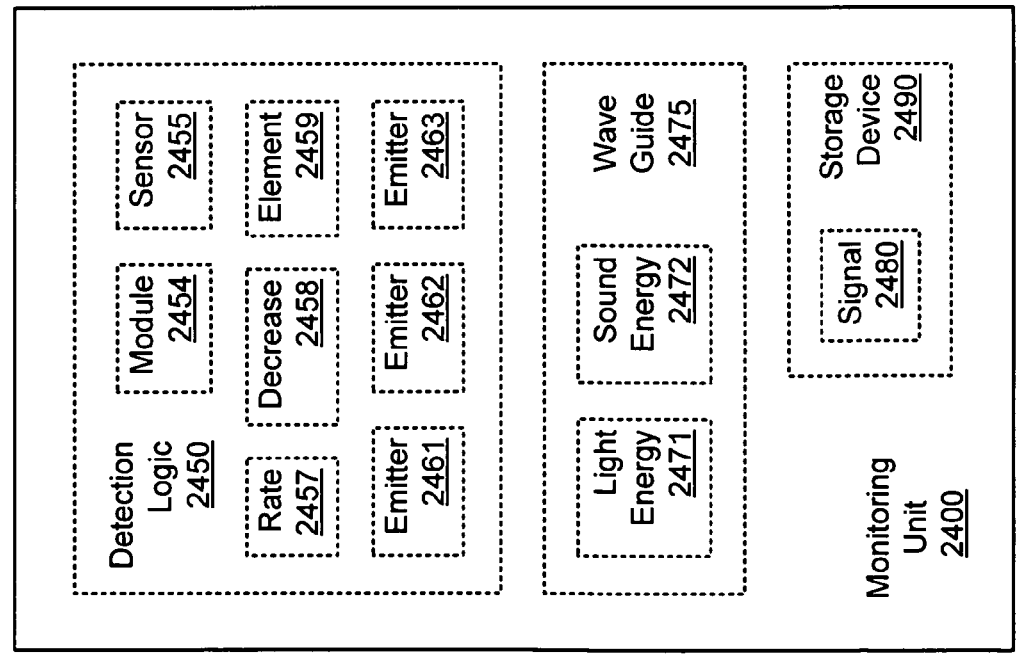

With reference now to FIG. 24, shown is a monitoring unit 2400 in which one or more technologies may be implemented, comprising one or more instances of detection logic 2450 and/or storage devices 2490 configured for handling one or more signals 2480. In some contexts, such signals are manifested as light energy 2471 and/or sound energy 2472 passing to or from a subject region via one or more wave guides 2475. In some contexts, one or more sensors 2455 or other modules 2451 of detection logic 2450 may permit a rate 2457, decrease 2458, or other such element 2459 to be detected in response, for example, to real-time data 1781. Alternatively or additionally, detection logic 2450 may include or otherwise interact with one or more emitters 2461, 2462, 2463 as described below.

Some variants include one or more modules 2451 of detection logic 2450 comprising circuitry for detecting a (thermal or other) normalization rate decrease. This can occur, for example, in a context in which module 2451 detects that region 2521 does not return to a normal parametric range as quickly as it normally should, in response to local aberrations. This can occur, for example, in a context in which module 2501 remains in place long enough to permit module 2451 to establish a normalcy range relating to such (unsigned) rates of normalization for region 2521, and in which such a rate apparently decreases several times over an interval of a minute, an hour, a day, or more. In some contexts in which a limb has been affected by an environmental or other thermal disturbance, for example, module 2451 may effectively characterize one or more rates at which the temperature distribution of the region returns toward an equilibrium status. Alternatively or additionally, detection logic 2450 may include or otherwise operate in conjunction with a (heating and/or cooling) modulation element 2459 (in module 2501, e.g.) so that an apparent decrease 2458 in a computed normalization rate 2457 may be distinguished from an environmental trend or otherwise confirmed as an apparent symptom of worsening circulation.

An embodiment provides a monitoring unit 2400 configured as a positioning structure configured to be worn by a healthcare recipient, a sensor 2455 or other module 2451 of detection logic 2450 supported by the positioning structure; one or more emitters 2461, 2462 or other output devices supported by the positioning structure and configured to transmit one or more signals from the detection logic 2450 (as light energy 2471 or sound energy 2472, e.g.); and one or more other emitters 2462, 2463 comprising output devices supported by the positioning structure and configured to transmit at least some health-related rates 2457 or other such information to a vicinity of the healthcare recipient.

An embodiment provides a physiological support 2510 or other positioning structure configured to be worn on at least a limb 2530 of a healthcare recipient, one or more modules 2503 configured as receivers supported by the positioning structure and configured to receive wireless or other signals 2570, and at least one emitter 2515 (configured as a speaker or other wireless-signal output device, e.g.) supported by the positioning structure and configured to transmit measurements or other health-related information responsive to signal 2570 and to sensor data from one or more sensor-containing modules 2501, 2502 in proximity to the healthcare recipient. In some contexts, for example, such sensor data 2635, 764 can originate from the same or other articles worn by the healthcare recipient.

Figure 25:
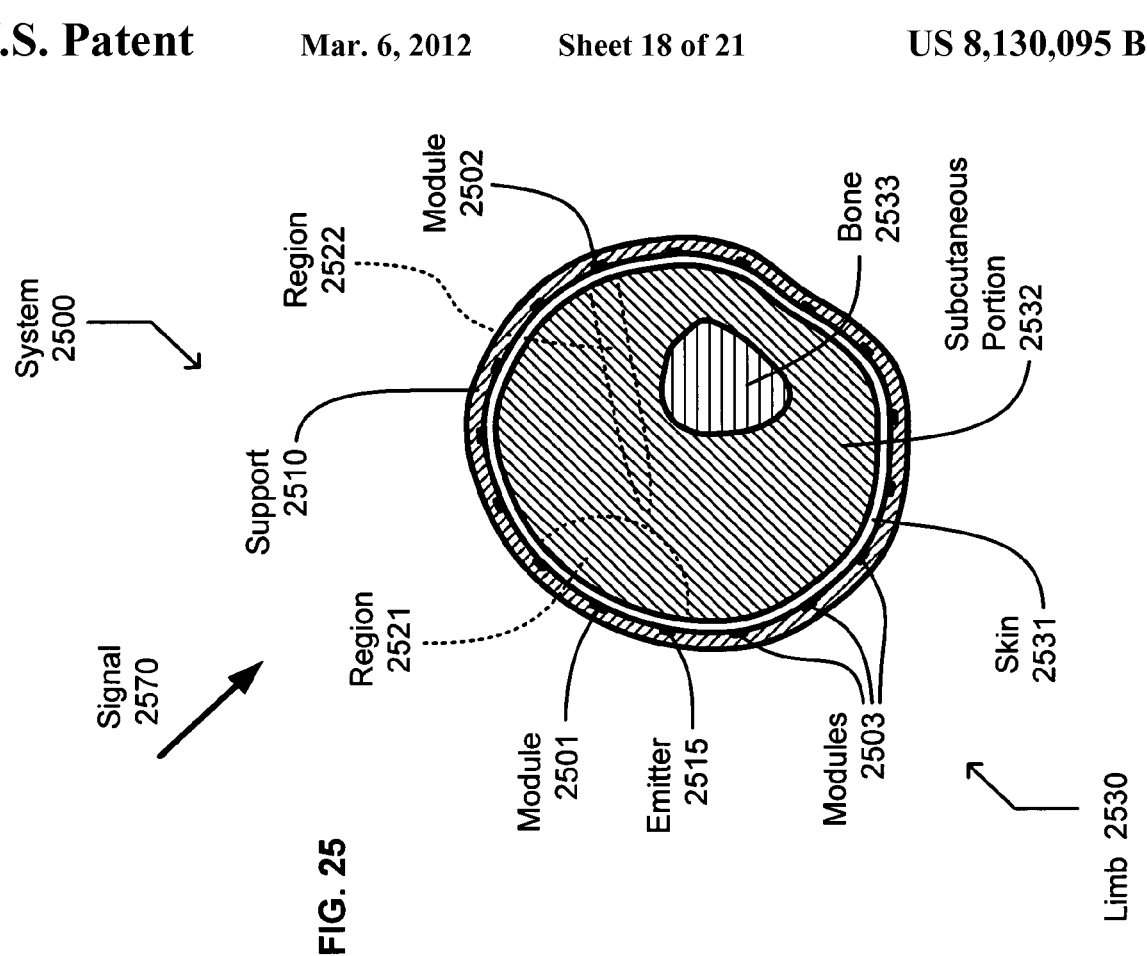

With reference now to FIG. 25, shown is a system 2500 in which one or more technologies may be implemented. System 2500 comprises an elastic or other physiological support 2510 wrapped around a subject's limb 2530 and holding several modules 2501, 2502, 2503 in contact with the subject's skin 2531, optionally via a liquid-containing contact-enhancement medium. Some of these modules 2501, 2502, 2503 may (a) position a sensor at least in a vicinity of the healthcare recipient for a period of more than an hour and/or (b) implement a receiver for receiving signal 2570 as described herein. In some contexts, for example, bandages or other such physiological supports 2610 as described below may implement system 2500. In some implementations, for example, such articles may safely remain in place for a day or longer.

In some variants, any of modules 2501, 2502, 2503 may implement one or more sensors of local modules 1420, 1550, 1610 configured to provide one or more indications of sensor data captured at different times. Such data may indicate, for example, whether one or more regions 2521, 2522 of limb 2530 exhibits one or more clotting symptoms across a period of several hours, a week, or longer. In some contexts, such data may be obtained (a) without further involvement of a caregiver and/or (b) from about the same position(s) as a prior sensing event. Alternatively or additionally, such modules may include one or more emitters 2515 operable for facilitating a detection of a bone 2533 or other subcutaneous portion 2532 of limb 2530. Other such embodiments are described above, for example, with reference to FIGS. 1-9.

Figure 26:
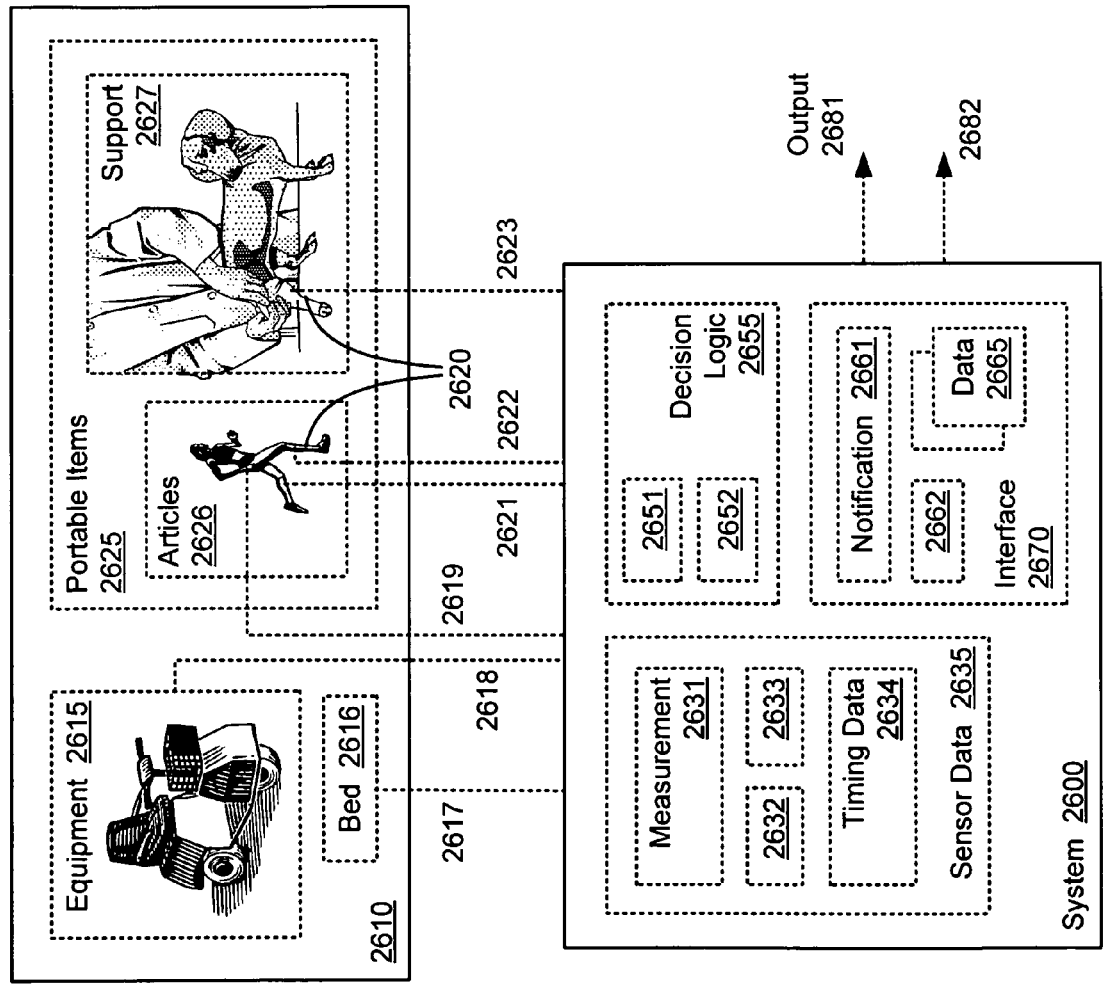

With reference now to FIG. 26, shown is a structure 2610 operable in conjunction with system 2600, in which one or more technologies may be implemented. Structure 2610 may include one or more items of transportation or other equipment 2615, beds 2616, and/or handheld or other portable items 2625. Such items may include hosiery, adhesive patches, or other such articles 2626; bandages or other supports 2627; or other such structures as described herein comprising one or more elements 2620 configured to provide information to and/or about such healthcare recipients.

In some variants, for example, system 2600 may comprise decision logic 2655 and/or interfaces 2670 operable for receiving or otherwise handling sensor data 2635 such as measurements 2631, timing data 2634, or other data 2632, 2633 as described herein. System 2600 may receive such information 2621, 2622, 2623 or otherwise interact with such structures 2610 via one or more intermittent or other data paths 2617, 2618, 2619. As described herein, decision logic 2655 may use some or all of such temperatures 2651 or other data 2652 as described herein, such as for causing module 2662 or other logic to configure or route notification 2661 or other data 2665 to one or more outputs 2681, 2682.

An embodiment provides a medical or veterinary system including a garment, portable item 2625, or other physiological support 2510 configured for bearing and/or surrounding some or all of a healthcare recipient. In some variants, for example, the system may include a cast, elastic wrapping, support hose, a sling, or other such structures (wearable by a human or other healthcare recipient, in some cases) for which supporting a subject's body part is not merely an incidental effect. Such systems may likewise include a monitoring unit 2400 or other device configured for communication, battery recharging, data synchronization, or other such support functions, for example, in a healthcare facility or home.

In some embodiments, the support(s) may contain or otherwise include circuitry for sensing a local temperature or other intensive property of tissue at an extremity or other body part directly. Alternatively or additionally, such sensing circuitry may derive such a value, such as by computing a ratio of estimates of two extensive properties of the healthcare recipient's limb. In some contexts, moreover, a signal-to-noise ratio (SNR) of such sensing may be increased by subtracting or otherwise mitigating an effect from skin or other external body portions, an effect from bones or other hard structures, an effect from an artificial or (prior) normal condition of the healthcare recipient, or other effects unrelated to the vasculature and/or to any meaningful intensive property trend.

In some variants, for example, a suitable threshold for a first potential trend may be on the order of 2-20 minutes or hours. Such trends may include indications of rapid local clotting, of a hemodynamic instability, or of other such imminent threats, for example. Alternatively or additionally, a suitable threshold for plaque accumulation or other such (more gradual) trends may be on the order of 1-3 days or months.

Figure 27:
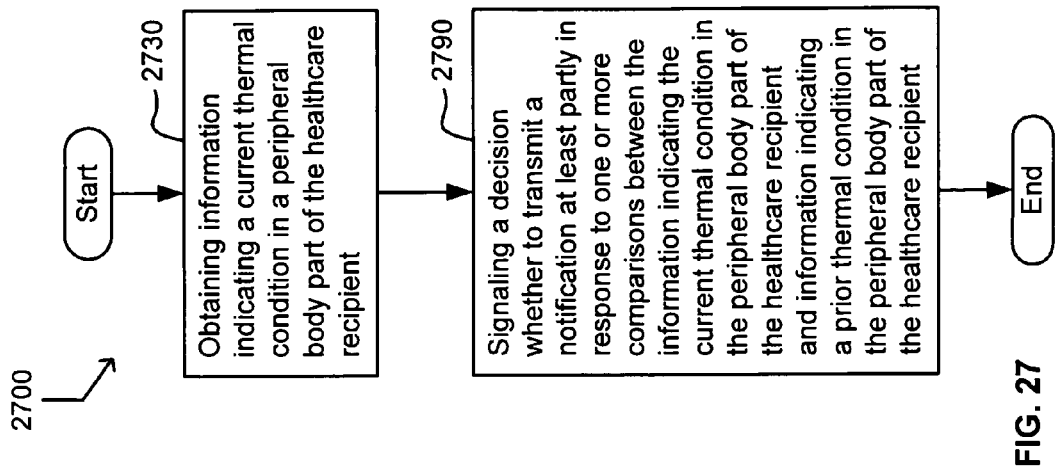
FIG. 27 depicts a high-level logic flow of an operational process.

With reference now to FIG. 27, shown is a flow 2700 comprising operation 2730—obtaining information indicating a current thermal condition in a peripheral body part of the healthcare recipient (e.g. decision logic 2655 receiving one or more temperatures 2651 or other such information 2621, 2622, 2623 via one or more portable items 2625 or other equipment 2615 within a proximity of the healthcare recipient). This can occur, for example, in a context in which system 2600 implements or otherwise interacts with such structures 2610, such as by one or more conduits or other signal paths 2617, 2618, 2619. In some variants, for example, decision logic 2655 may reside within one or more worn articles 2626, a bed 2616, or other equipment 2615 configured to support some or all of a healthcare recipient. Alternatively or additionally, one or more such structures 2610 may comprise or receive data from one or more implanted or other sensors and/or related circuitry as described above with reference to FIGS. 14-17. Such physical components may likewise incorporate or interact one or more instances of interface 2670 operable for interacting with (some) such patients or other parties, such as by performing operation 2790.

Operation 2790 describes signaling a decision whether to transmit a notification at least partly in response to one or more comparisons between the information indicating the current thermal condition in the peripheral body part of the healthcare recipient and information indicating a prior thermal condition in the peripheral body part of the healthcare recipient (e.g. interface 2670 directing one or more notifications 2661 to one or more outputs 2681 corresponding to recipients who have requested or may otherwise benefit from such timely information). This can occur, for example, in a context in which decision logic 2655 has addressed the notifications or otherwise selected the output(s) 2681 according to one or more expert-defined thresholds or other criteria as described herein. In some variants, for example, a recipient or other managing entity associated with output 2682 may choose a more extreme temperature or other threshold as a cutoff in response to receiving an excessive number of notifications that are not actionable. Alternatively or additionally, such an entity may likewise choose a mode of transmission, an inclusion of data 2665, or some other aspect of configuring notification 2661 in response to a recipient's indication of availability as described herein.

With reference now to FIG. 28, there are shown several variants of the flow 2700 of FIG. 27. Operation 2730—obtaining information indicating a current thermal condition in a peripheral body part of a healthcare recipient—may (optionally) include one or more of the following operations: 2835 or 2837. In some embodiments, variants of operation 2730 may be performed by one or more instances of detection logic 1240, 2240 or other such data reception or distillation logic as described herein. Operation 2790—signaling a decision whether to transmit a notification at least partly in response to one or more comparisons between the information indicating the current thermal condition in the peripheral body part of the healthcare recipient and information indicating a prior thermal condition in the peripheral body part of the healthcare recipient—may include one or more of the following operations: 2891, 2893, 2896 or 2899. In some embodiments, variants of operation 2790 may be performed by one or more instances of detection logic 120, 710, 1240; or other such processing and/or communication components. Alternatively or additionally, flow 2700 may be performed in a context as described above.

Operation 2835 describes determining that the information apparently manifests the current thermal condition in the peripheral body part of the healthcare recipient (e.g. evaluation module 2252 identifying abnormal-temperature-indicative data 2291 received from one or more components of local module 2232 and normal-temperature-indicative data 2292 received from local module 2231). This can occur, for example, in a context in which configuration module 2242 and evaluation module 2252 jointly perform operation 2730; in which other components of detection logic 2240 perform operation 2790; in which evaluation module 2252 implicitly treats such data 2291-2296 as "current" and "spatially separated" for diagnostic purposes; in which at least two such local modules 2231, 2232 each instantiate local module 1610 of FIG. 16 (local to healthcare recipient 2220, e.g.); and in which local module 2232 detects two or more physical phenomena as described herein from peripheral body part 2222. In some variants, for example, one or more elements 2233 of such local modules 2231, 2232 may comprise respective instances of temperature sensors 1612 or other sensors as shown in FIG. 16. Alternatively or additionally, some or all such data 2291-2296 may (optionally) include (a) color-indicative or other measurement data 2294; (b) timestamps 1644, coordinates 1645, anatomical descriptions, shape data, or other such temporal or spatial indices 1646; and/or (c) pathology profile data 2295; or other such diagnostically useful information.

In light of teachings herein, numerous existing techniques may be applied for determining a data object type, format, or other indication whether data may be evaluated as described herein without undue experimentation. See, e.g., U.S. Pat. No. 7,296,238 ("Method and apparatus for triggering automated processing of data"); U.S. Pat. No. 7,269,718 ("Method and apparatus for verifying data types to be used for instructions and casting data types if needed"); U.S. Pat. No. 7,263,688 ("Method and apparatus for dynamic data-type management"); U.S. Pat. No. 7,020,666 ("System and method for unknown type serialization"); U.S. Pat. No. 7,016,601 ("Method and apparatus for storing different types of data on the same storing medium"); U.S. Pat. No. 6,738,769 ("Sorting multiple-typed data"); U.S. Pat. No. 6,621,506 ("Applying operations to selected data of different types"); U.S. Pat. No. 6,170,997 ("Method for executing instructions that operate on different data types stored in the same single logical register file"); U.S. Pat. No. 5,718,247 ("Apparatus and process for interactive psychotherapy").

Operation 2837 describes extracting a portion of detected information as the information indicating the current thermal condition in the peripheral body part of the healthcare recipient (e.g. module 2302 of extraction logic 2310 selectively including one or more measurements 2317 or ratios 2334 or other measurement-based computations 2336 extracted from output 2312 of sensors or other detection circuitry as described herein). This can occur, for example, in a context in which a sampling 2314, a distillation 2315, one or more measurements 2316, 2317 of particular interest, or some other subset of such output 2312 is logged or otherwise retained for comparison and/or included in one or more notifications as described herein. In some variants, for example, such a notification may include a blood pressure measurement 2318, a range or other type identifier 2319, and/or other such extracted information 2320. Alternatively or additionally, such a notification may include advice 2332, a recipient-appropriate translation, or other such categorical information 2330 extracted from a database 2381 or other such secondary information source 2380 using the extracted information 2320, for example, as a search term.

In light of teachings herein, numerous existing techniques may be applied for selectively retaining probative data portions or otherwise sampling or sifting detected information as described herein without undue experimentation. See, e.g., U.S. Pat. No. 7,343,305 ("Method and system for recording carious lesions"); U.S. Pat. No. 7,325,297 ("Automatic assembly machine for mounting bearings onto motors"); U.S. Pat. No. 7,280,992 ("Method for processing medically relevant data"); U.S. Pat. No. 7,254,425. ("Method for detecting artifacts in data"); U.S. Pat. No. 7,076,436 ("Medical records, documentation, tracking and order entry system"); U.S. Pat. No. 6,826,578 ("Method, system, and computer product for collecting and distributing clinical data for data mining"); U.S. Pat. No. 6,611,846 ("Method and system for medical patient data analysis").

Operation 2891 describes deciding whether to transmit the notification responsive to whether any of the one or more comparisons indicate an abnormal temperature change in the peripheral body part of the healthcare recipient (e.g. module 1243 of detection logic 1240 sounding an alarm only if comparison result 1255 indicates that any body part of a healthcare recipient 550, 950 is excessively hot or cold). This can occur, for example, in a context in which detection logic 1240 is wirelessly or otherwise coupled to respective portions of gown 562; in which module 1241 and/or responsive logic 1250 perform operation 2730; in which detection logic 1240 performs operation 2790; in which monitoring apparatus 1260 resides in a vicinity 555 of healthcare recipient 550 and in which a nearby person may be pre-trained and/or contemporaneously guided to provide adequate and timely aid. Such aid may include talking with or positioning a healthcare recipient; helping a healthcare recipient to administer medications; obtaining a defibrillator, ECG monitor, or other such therapeutic or diagnostic instruments; or contacting a physician or ambulance for more extreme situations. In some variants, for example, one or more modules 1251 of responsive logic 1250 may enable such detection logic periodically or otherwise in response to detected events. Alternatively or additionally, an item of clothing or other wearable article may include one or more instances of local module 1610 of FIG. 16 operable for transmitting comparison results, measurement data, or decisions as described herein.

Operation 2893 describes signaling the decision by transmitting the notification to a portable interface (e.g. channel 1150 transmitting one or more notifications 1141, 1142 as described herein via one or more antennas 1149 to one or more wearable or other portable interfaces 1180, 2160, 2180 or other destinations). This can occur, for example, in a context in which such a transmission results from one or more hybrid-data decisions 1131 or other thermally-dependent decisions 1132 and in which one or more controllers as described herein include one or more implementations of local module 1110. In some variants, for example, some or all of the content 1144 of such a notification may depend upon a type 1133 of one or more such interfaces or other destinations 1135. Alternatively or additionally, such a decision may be signaled to a display element 1136 or other configurable feature local to local module 1110.

Operation 2896 describes ranking a higher-priority destination and a lower-priority destination for the notification (e.g. module 2171 ranking one or more nearby interfaces 2160 with a higher-priority category 2144 than that of one or more interfaces 2180 of network 2190). This can occur, for example, in a context in which a notification 2168 is first routed to a healthcare recipient or other higher-priority destination and in which a related notification is routed to another party a few minutes or hours later in the event that module 2172 does not receive input 2134 from the higher-priority destination. In some variants, for example, such input may include an acknowledgment that someone has received the notification. Alternatively or additionally, any such decisions, notifications, or determinants may be logged to other destinations, such as logging module 2185.

Operation 2899 describes signaling the decision whether to transmit the notification partly in response to auditory information from the healthcare recipient (e.g. local module 1110 updating a party partly in response to recognition module 2281 indicating one or more comparison results 2262 and partly in response to recognition module 2283 indicating a recognition of one or more phrases or other patterns 2273, 2274 in speech or other auditory information 2241 from healthcare recipient 2220). This can occur, for example, in a context in which such auditory information 2241 indicates that healthcare recipient 2220 may currently be impaired and in which at least one such result 2262 of comparing abnormal-temperature-indicative data 2291 with historical or other filtering data indicates that a hot zone of peripheral body part 2222 has become measurably hotter and that peripheral body part 2221 has apparently remained in a normal condition. In some contexts, for example, such normality may be inferred from abnormal-temperature-indicative data 2291 not referring to part 2221 and/or not coming from one or more local modules 2231 in a vicinity of part 2221. Alternatively or additionally, the decision may depend upon one or more other determinants such as (a) whether a current notification 1142 differs from a prior notification 1141; (b) whether interface 1180 indicates that one or more recipients are apparently online; (c) whether any new comparison result reflects a new, unrecognized, and/or other urgent situation; or other criteria as described herein.

In light of teachings herein, numerous existing techniques may be applied for recognizing words or other auditory patterns as described herein without undue experimentation. See, e.g., U.S. Pat. No. 7,257,531 ("Speech to text system using controlled vocabulary indices"); U.S. Pat. No. 6,990,455 ("Command and control using speech recognition for dental computer connected devices"); U.S. Pat. No. 6,934,579 ("Anaesthesia control system"); U.S. Pat. No. 6,804,654 ("System and method for providing prescription services using voice recognition"); U.S. Pat. No. 6,785,358 ("Voice activated diagnostic imaging control user interface"); U.S. Pat. No. 6,629,937 ("System for processing audio, video and other data for medical diagnosis and other applications"); U.S. Pat. No. 5,335,313 ("Voice-actuated, speaker-dependent control system for hospital bed"); U.S. Pat. No. 5,262,669 ("Semiconductor rectifier having high breakdown voltage and high speed operation").

With reference now to FIG. 29, there are shown several variants of the flow 2700 of FIG. 27 or 28. Operation 2730—obtaining information indicating a current thermal condition in a peripheral body part of a healthcare recipient—may (optionally) include one or more of the following operations: 2931 or 2939. In some embodiments, variants of operation 2730 may be performed by one or more instances of local modules 1420, 1550, 1610, 1790, 2231, 2232 or other modules 2120 configured to handle sensor data; decision logic 1875, 1995; or other components configured to handle such status information. Operation 2790—signaling a decision whether to transmit a notification at least partly in response to one or more comparisons between the information indicating the current thermal condition in the peripheral body part of the healthcare recipient and information indicating a prior thermal condition in the peripheral body part of the healthcare recipient—may include one or more of the following operations: 2992, 2995, 2997 or 2998. In some embodiments, variants of operation 2790 may be performed by one or more instances of distribution logic; notification logic 2175; or other such control or communication components. Alternatively or additionally, flow 2700 may be performed in a context as described above.

Operation 2931 describes obtaining an optical image of the peripheral body part of the healthcare recipient of the information indicating the current thermal condition in the peripheral body part of the healthcare recipient (e.g. module 2120 receiving image 2131 from infrared sensor 1623 or image 2132 from another optical sensor 1625 from a position adjacent a patient's body part). This can occur, for example, in a context in which a patient or caregiver positions a charge-coupled device or similar image capture mechanism in a vicinity of the body part to monitor a growth or other optically detectable phenomenon, optionally in a manner that captures one or more isotherm-indicative shapes. In some variants, for example, a sensor array comprising infrared-sensitive elements may be used for implementing such data capture. Alternatively or additionally, other radiant-energy-sensitive and/or other elements as described herein may be used for sensing diagnostically useful information contemporaneously relating to the same part of the healthcare recipient.

Operation 2939 describes detecting that the information indicates normalcy as the current thermal condition in the peripheral body part of the healthcare recipient (e.g. one or more modules 1877 of decision logic 1876 indicating normalcy in response to receiving a high-enough and/or low-enough numerical value 1887 directly or indirectly from one or more sensors 1827 operable for detecting a temperature at an extremity of healthcare recipient 1820). This can occur, for example, in a context in which healthcare recipient 1820 rests upon or otherwise interacts with structure 1825, in which decision logic 1876 is capable of detecting and indicating whether value 1887 is too far from a normal temperature, and in which transmitter 1880 is operable for performing operation 2790. In some variants, for example, module 1877 may employ this information as a factor in deciding whether to transmit a notification to user interface 1852 or to other destinations. Alternatively or additionally, in various implementations as described herein, structure 1825 may include one or more instances of response logic or other circuitry operable for responding conditionally to an identifier 1823 of a healthcare recipient or other determinants in detected data 1822.

In light of teachings herein, numerous existing techniques may be applied for detecting statistical, anatomical, or other potentially useful thermal aberrations in light of other circumstances as described herein without undue experimentation. See, e.g., U.S. Pat. No. 7,340,293 ("Methods and apparatus for a remote noninvasive technique to detect core body temperature in a subject via thermal imaging"); U.S. Pat. No. 7,226,426 ("Apparatus and method for the detection and quantification of joint and tissue inflammation"); U.S. Pat. No. 6,963,772 ("User-retainable temperature and impedance monitoring methods and devices"); U.S. Pat. No. 6,757,412 ("System and method for helping to determine the condition of tissue"); U.S. Pat. No. 6,126,614 ("Apparatus and method for analysis of ear, pathologies by detecting fluid in the ear measuring body temperature and/or determining a characteristic of a fluid"); U.S. Pat. No. 6,023,637 ("Method and apparatus for thermal radiation imaging"); U.S. Pat. No. 5,999,842 ("Functional thermal imaging apparatus"); U.S. Pat. No. 5,997,472 ("Endodiagnostic method using differential thermal relaxation and IR imaging").

Operation 2992 describes including auditory data with the notification (e.g. one or more modules 2171-2174 of notification logic 2175 configuring notification 2168 to include speech 2164 or other audible data with other content 2165 of notification 2168 delivered to one or more interfaces 2160, 2180). This can occur, for example, in a context in which notification logic 2175 performs at least operation 2790 and in which one or more users or devices have indicated a telephone, computer speaker, or other interface facility for handling such data. In some variants, for example, output 2137 from a microphone or other sensor 2124 may first be detected as speech, a heartbeat or other audible metabolic indicator, or other device-detectable phenomena in a healthcare recipient's vicinity. Alternatively or additionally, content 2165 provided with a notification 2168 may include one or more instances of translated or other programmatic notifications, for example, suitable for remote delivery at a speaker-containing interface 2180.

In light of teachings herein, numerous existing techniques may be applied for amplifying, recording, translating, selecting, or otherwise facilitating an inclusion of potentially useful auditory data as described herein without undue experimentation. See, e.g., U.S. Pat. No. 7,313,529 ("Portable extender for data transmission within a medical device communication system"); U.S. Pat. No. 7,291,111 ("Apparatus and method for non-invasive diagnosing of coronary artery disease"); U.S. Pat. No. 6,944,497 ("System and method of treating stuttering by neuromodulation"); U.S. Pat. No. 6,878,117 ("Handheld sensor for acoustic data acquisition"); U.S. Pat. No. 6,629,937 ("System for processing audio, video and other data for medical diagnosis and other applications"); U.S. Pat. No. 6,582,379 ("Apparatus and method of measuring the flow of a liquid, in particular urine, from a patient"); U.S. Pat. No. 6,126,614 ("Apparatus and method for analysis of ear pathologies by detecting fluid in the ear, measuring body temperature and/or determining a characteristic of a fluid"); U.S. Pat. No. 6,014,626 ("Patient monitoring system including speech recognition capability").

Operation 2995 describes selecting one or more destinations for the notification (e.g. distribution module 2350 selecting one or more destinations 2341, 2342 using client list 2367 or other determinants as described herein). This can occur, for example, in a context in which a wearable article implements system 2300 (of FIG. 23) and in which one or more preferences of a client system, member, or other interested party are registered for notification via subscriber profile 2361 or other such indication. In some variants, for example, a nurse may associate one or more healthcare recipient identifiers with a wearable article and/or a notification of changes in symptomatic parameters signaled by indication 1256 and may receive a notification 2338 via a wearable or other local module 1270, in some variants, in response to a detection of one or more symptoms of interest as described herein. Alternatively or additionally, a clinician 1310 or other interested party may receive such a notification 2338 selectively, for example via stationary module 1350. In a variety of contexts as described herein, such implementations can facilitate a faster therapeutic response.

In light of teachings herein, numerous existing techniques may be applied for the selection of one or more recipients for medical or other notifications as described herein without undue experimentation. See, e.g., U.S. Pat. No. 7,333,014 ("Notifying users of device events in a networked environment"); U.S. Pat. No. 7,310,615 ("Financial data reporting system with alert notification feature and free-form searching capability"); U.S. Pat. No. 7,308,246 ("Emergency notification system and emergency notification device"); U.S. Pat. No. 7,233,781 ("System and method for emergency notification content delivery"); U.S. Pat. No. 7,180,415 ("Safety/security alert system"); U.S. Pat. No. 7,003,525 ("System and method for defining, refining, and personalizing communications policies in a notification platform"); U.S. Pat. No. 6,834,306 ("Method and apparatus for notifying a user of changes to certain parts of web pages"); U.S. Pat. No. 6,442,241 ("Automated parallel and redundant subscriber contact and event notification system"); U.S. Pat. No. 6,177,873 ("Weather warning apparatus and method"); U.S. Pat. No. 6,014,346 ("Medical timer/monitor and method of monitoring patient status").

Operation 2997 describes including thermal-decrease-size-indicative information with the notification (e.g. module 2662 including a number of degrees or other data 2665 received as information 2622, 2623 from one or more portable items 2625 indicating how much a healthcare recipient's appendage has apparently cooled). This can occur in a context in which such cooling results from a wound dressing or other article significantly impairing a healthcare recipient's circulation, for example, or in which such cooling signifies a return to normalcy from an overly-hot condition. In some contexts, for example, a notification recipient may respond with timely advice for treating the healthcare recipient's leg in response to such quantified notification. Alternatively or additionally, in some contexts, such information may warrant a change in how the healthcare recipient is monitored, such as by decreasing vigilance and/or by monitoring systemic, environmental, or other information 2621 relating to a healthcare recipient as described herein.

Operation 2998 describes including spatial-size-indicative information with the notification (e.g. module 2174 of notification logic 2175 including one or more of a scaling factor 2142 or other areal indicator 2143, photographs or other images 2131, 2132, a volumetric or shape-descriptive category 2144, and/or other such information included in or appended to content 2165 of notification 2168). This can occur, for example, in a context in which interface 2160 performs operation 2730, in which module 2173 decides whether to transmit the notification, in which notification logic 2175 performs operation 2790, and in which a healthcare recipient cannot communicate such information and/or otherwise address a pathology. In some variants, for example, module 2173 signals in the affirmative if a hot zone 2139 of an image 2132 is larger than threshold 2145. Alternatively or additionally, the decision may likewise depend upon one or more of an iteration count 2141 or other indicator of duration, user input 2134, a concentration or other output 2137 from an electrochemical sensor 1648 (of module 2120, e.g.), and/or other determinants 2150 as described herein.

In light of teachings herein, numerous existing techniques may be applied for shape recognition or other analyses of spatial attributes as described herein without undue experimentation. See, e.g., U.S. Pat. No. 7,346,205 ("System and method for rapidly identifying pathogens, bacteria and abnormal cells"); U.S. Pat. No. 7,340,077 ("Gesture recognition system using depth perceptive sensors"); U.S. Pat. No. 7,331,667 ("Iris pattern recognition and alignment"); U.S. Pat. No. 7,327,861 ("Organism authenticating apparatus"); U.S. Pat. No. 7,317,821 ("Automatic abnormal tissue detection in MRI images"); U.S. Pat. No. 7,242,807 ("Imaging of biometric information based on three-dimensional shapes"); U.S. Pat. No. 7,184,580 ("Fingerprint scar recognition method and apparatus"); U.S. Pat. No. 6,840,117 ("Patient monitoring system employing array of force sensors on a bedsheet or similar substrate"); U.S. Pat. No. 6,675,040 ("Optical object tracking system"); U.S. Pat. No. 6,529,759 ("Method for mapping internal body tissue").

Some variants include one or more modules 118, 331 for recognizing one or more queries 621, gestures 622, images 623, symbols 624, call signals 625, authorizations 626, notifications 627 or other such patterns of user input 620 in data 650 from one or more sensors in a healthcare recipient's vicinity 555, 955. This can occur, for example, in a context in which such circuitry implements or otherwise interacts with one or more local modules 1420, 1550, 1610, 1790 within or near the healthcare recipient.

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Various aspects of the subject matter described herein are set out in the following numbered clauses:

1. A system comprising:
a positioning structure configured to be worn by a healthcare recipient;
a movement detector supported by the positioning structure;
a first output device supported by the positioning structure and configured to transmit at least a signal from the movement detector; and
a second output device supported by the positioning structure and configured to transmit at least some health-related information in a vicinity of the healthcare recipient.

2. The system of clause 1, further comprising:
a receiver supported by the positioning structure; and
a stationary module operable for transmitting another signal to the receiver.

3. The system of clause 2 in which the stationary module comprises:
a camera configured to obtain an image of the second output device.

4. The system of clause 1, further comprising:
circuitry for causing a notification to be routed to at least one of the first output device or the second output device.

5. The system of clause 1, further comprising:
circuitry for invoking at least one of the first output device, the second output device, or a third output device selected in response to a configuration parameter.

6. The system of clause 1, further comprising:
circuitry for including at least some medical history data in the health-related information.

7. The system of clause 1, further comprising:
circuitry for including at least some real-time data in the health-related information.

8. The system of clause 1, further comprising:
circuitry for signaling at least a clot-reducing agent in response to an apparent circulatory degradation.

9. The system of clause 1, further comprising:
circuitry for transmitting data indicating one or more concentrations of a nutrient or medication.

10. The system of clause 1, further comprising:
circuitry for detecting thermal data.
11. The system of clause 1, further comprising:
circuitry for transmitting one or more swelling indications.
12. The system of clause 1, further comprising:
one or more sensors adjacent a body part of the healthcare recipient.
13. The system of clause 1, further comprising:
a sensor supported by the positioning structure and configured to generate sensor data; and
circuitry for recognizing a pattern in the sensor data.
14. The system of clause 13, further comprising:
circuitry for detecting one or more indications of normalcy in the sensor data.
15. The system of clause 13, further comprising:
circuitry for indicating one or more conditional notifications responsive to the sensor data.
16. The system of clause 13, further comprising:
circuitry for obtaining a turbulence-indicative auditory value as a flow-change-indicative measurement.
17. The system of clause 13, further comprising:
circuitry for performing a comparison using an updated normalcy threshold.
18. The system of clause 13, in which the positioning structure comprises:
the positioning structure mechanically supporting at least a portion of the circuitry for recognizing the pattern in the sensor data.
19. The system of clause 1, in which the positioning structure comprises:
clothing.
20. The system of clause 1, in which the positioning structure comprises:
one or more of a cuff, a sleeve, or a wristband.
21. The system of clause 1, in which the positioning structure comprises:
one or more of eyewear, an earpiece, or a headpiece.
22. The system of clause 1, in which the positioning structure comprises:
the positioning structure configured to surround a portion of the healthcare recipient.
23. The system of clause 1, in which the movement detector comprises:
at least one of an accelerometer or a proximity sensor.
24. The system of clause 1, further comprising:
a user interface operable to receive input from the healthcare recipient.
25. The system of clause 24, in which the user interface comprises:
a sonic sensor.
26. The system of clause 24, in which the user interface comprises:
a touchscreen.
27. The system of clause 24, in which the user interface comprises:
circuitry for presenting content provided by a healthcare facility in the healthcare facility.
28. The system of clause 1, in which the second output device comprises:
circuitry for transmitting a verification.
29. The system of clause 1, in which the second output device comprises:
circuitry for transmitting a resource status indication.
30. The system of clause 1, in which the second output device comprises:
circuitry for transmitting other information to one or more other recipients.
31. The system of clause 1, in which the second output device comprises:
circuitry for transmitting likelihood-indicative data.
32. The system of clause 1, in which the second output device comprises:
circuitry for transmitting one or more limb pain indications.
33. The system of clause 1, further comprising:
circuitry for obtaining information indicating a current thermal condition in a peripheral body part of the healthcare recipient.
34. The system of clause 33 in which the circuitry for obtaining information indicating a current thermal condition in a peripheral body part of the healthcare recipient comprises:
circuitry for determining that the information apparently manifests the current thermal condition in the peripheral body part of the healthcare recipient.
35. The system of clause 33 in which the circuitry for obtaining information indicating a current thermal condition in a peripheral body part of the healthcare recipient comprises:
circuitry for extracting a portion of detected information as the information indicating the current thermal condition in the peripheral body part of the healthcare recipient.
36. The system of clause 33 in which the circuitry for obtaining information indicating a current thermal condition in a peripheral body part of the healthcare recipient comprises:
circuitry for obtaining an optical image of the peripheral body part of the healthcare recipient of the information indicating the current thermal condition in the peripheral body part of the healthcare recipient.
37. The system of clause 33 in which the circuitry for obtaining information indicating a current thermal condition in a peripheral body part of the healthcare recipient comprises:
circuitry for detecting that the information indicates normalcy as the current thermal condition in the peripheral body part of the healthcare recipient.
38. The system of clause 33, further comprising:
circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.
39. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for deciding whether to transmit the notification responsive to whether any of the one or more comparisons indicate an abnormal temperature change in the peripheral body part of the healthcare recipient.
40. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision by transmitting the notification to a portable interface.

41. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for ranking a higher-priority destination and a lower-priority destination for the notification.

42. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision whether to transmit the notification partly in response to auditory information from the healthcare recipient.

43. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including auditory data with the notification.

44. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for selecting one or more destinations for the notification.

45. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including thermal-decrease-size-indicative information with the notification.

46. The system of clause 38 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including spatial-size-indicative information with the notification.

47. A system comprising:
a positioning structure configured to be worn by a healthcare recipient;
a receiver supported by the positioning structure and configured to receive a wireless signal; and
a first output device supported by the positioning structure and configured to transmit at least some health-related information responsive to the wireless signal and to a status update relating to the healthcare recipient.

48. The system of clause 47, further comprising:
a stationary module operable for transmitting the wireless signal to the receiver.

49. The system of clause 47, further comprising:
a second output device supported by the positioning structure; and
circuitry for causing a notification to be routed to at least one of the first output device or the second output device.

50. The system of clause 47, further comprising:
circuitry for invoking at least one of the first output device or a second output device selected in response to a configuration parameter and to the wireless signal.

51. The system of clause 47, further comprising:
circuitry for including at least some medical history data in the health-related information.

52. The system of clause 47, further comprising:
circuitry for including at least some real-time data in the health-related information.

53. The system of clause 47, further comprising:
circuitry for signaling at least a clot-reducing agent in response to an apparent circulatory degradation.

54. The system of clause 47, further comprising:
circuitry for transmitting data indicating one or more concentrations of a nutrient or medication.

55. The system of clause 47, further comprising:
circuitry for detecting thermal data.

56. The system of clause 47, further comprising:
circuitry for transmitting one or more swelling indications.

57. The system of clause 47, further comprising:
an accelerometer supported by the positioning structure.

58. The system of clause 47, further comprising:
a proximity sensor supported by the positioning structure.

59. The system of clause 47, further comprising:
one or more sensors adjacent a body part of the healthcare recipient.

60. The system of clause 47, further comprising:
a sensor supported by the positioning structure; and
circuitry for recognizing a pattern in data from the sensor.

61. The system of clause 60, further comprising:
circuitry for detecting one or more indications of normalcy in the data from the sensor.

62. The system of clause 60, further comprising:
circuitry for indicating one or more conditional notifications responsive to the data from the sensor.

63. The system of clause 60, further comprising:
circuitry for obtaining a turbulence-indicative auditory value as a flow-change-indicative measurement.

64. The system of clause 60, further comprising:
circuitry for performing a comparison using an updated normalcy threshold.

65. The system of clause 60, in which the positioning structure comprises:
the positioning structure mechanically supporting at least a portion of the circuitry for recognizing the pattern in the data from the sensor.

66. The system of clause 47, in which the positioning structure comprises:
clothing.

67. The system of clause 47, in which the positioning structure comprises:
one or more of a cuff, a sleeve, or a wristband.

68. The system of clause 47, in which the positioning structure comprises:
eyewear.

69. The system of clause 47, in which the positioning structure comprises:
one or more of an earpiece or a headpiece.

70. The system of clause 47, in which the positioning structure comprises:
the positioning structure configured to surround a portion of the healthcare recipient.

71. The system of clause 47, in which the positioning structure comprises:
the output device configured to receive optical energy as the wireless signal.

72. The system of clause 47, further comprising:
a user interface operable to receive input from the healthcare recipient.

73. The system of clause 72, in which the user interface comprises:
a sonic sensor.

74. The system of clause 72, in which the user interface comprises:
a touchscreen.

75. The system of clause 72, in which the user interface comprises:
circuitry for presenting content provided by a healthcare facility in the healthcare facility.

76. The system of clause 47, in which the first output device comprises:
circuitry for transmitting one or more of a verification or a resource status indication.

77. The system of clause 47, in which the first output device comprises:
circuitry for transmitting other information to one or more other recipients.

78. The system of clause 47, in which the first output device comprises:
circuitry for transmitting the health-related information with one or more computations of cost.

79. The system of clause 47, in which the first output device comprises:
circuitry for transmitting likelihood-indicative data.

80. The system of clause 47, in which the first output device comprises:
circuitry for transmitting one or more limb pain indications.

81. The system of clause 47, further comprising:
circuitry for obtaining information indicating a current thermal condition in a peripheral body part of the healthcare recipient.

82. The system of clause 81 in which the circuitry for obtaining information indicating a current thermal condition in a peripheral body part of the healthcare recipient comprises:
circuitry for determining that the information apparently manifests the current thermal condition in the peripheral body part of the healthcare recipient.

83. The system of clause 81 in which the circuitry for obtaining information indicating a current thermal condition in a peripheral body part of the healthcare recipient comprises:
circuitry for extracting a portion of detected information as the information indicating the current thermal condition in the peripheral body part of the healthcare recipient.

84. The system of clause 81 in which the circuitry for obtaining information indicating a current thermal condition in a peripheral body part of the healthcare recipient comprises:
circuitry for obtaining an optical image of the peripheral body part of the healthcare recipient of the information indicating the current thermal condition in the peripheral body part of the healthcare recipient.

85. The system of clause 81 in which the circuitry for obtaining information indicating a current thermal condition in a peripheral body part of the healthcare recipient comprises:
circuitry for detecting that the information indicates normalcy as the current thermal condition in the peripheral body part of the healthcare recipient.

86. The system of clause 81, further comprising:
circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.

87. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for deciding whether to transmit the notification responsive to whether any of the one or more comparisons indicate an abnormal temperature change in the peripheral body part of the healthcare recipient.

88. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision by transmitting the notification to a portable interface.

89. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for ranking a higher-priority destination and a lower-priority destination for the notification.

90. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision whether to transmit the notification partly in response to auditory information from the healthcare recipient.

91. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including auditory data with the notification.

92. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for selecting one or more destinations for the notification.

93. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for including thermal-decrease-size-indicative information with the notification.

94. The system of clause 86 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for including spatial-size-indicative information with the notification.

95. A system comprising:

a positioning structure configured to be worn by a healthcare recipient;

a receiver supported by the positioning structure and configured to receive a wireless signal; and a first output device supported by the positioning structure and configured to present at least some health-related information responsive to the wireless signal and to a status update relating to the healthcare recipient.

96. The system of clause 95, further comprising:

a stationary module operable for transmitting the wireless signal to the receiver.

97. The system of clause 95, further comprising:

a second output device supported by the positioning structure; and circuitry for causing a notification to be routed to at least one of the first output device or the second output device.

98. The system of clause 95, further comprising:

circuitry for invoking at least one of the first output device or a second output device selected in response to a configuration parameter and to the wireless signal.

99. The system of clause 95, further comprising:

circuitry for including at least some medical history data in the health-related information.

100. The system of clause 95, further comprising:

circuitry for including at least some real-time data in the health-related information.

101. The system of clause 95, further comprising:

circuitry for signaling at least a clot-reducing agent in response to an apparent circulatory degradation.

102. The system of clause 95, further comprising:

circuitry for transmitting data indicating one or more concentrations of a nutrient or medication.

103. The system of clause 95, further comprising:

an accelerometer supported by the positioning structure.

104. The system of clause 95, further comprising:

one or more sensors adjacent a body part of the healthcare recipient.

105. The system of clause 95, further comprising:

a sensor supported by the positioning structure; and circuitry for recognizing a pattern in data from the sensor.

106. The system of clause 105, further comprising:

circuitry for detecting one or more indications of normalcy in the data from the sensor.

107. The system of clause 105, further comprising:

circuitry for indicating one or more conditional notifications responsive to the data from the sensor.

108. The system of clause 105, further comprising:

circuitry for obtaining a turbulence-indicative auditory value as a flow-change-indicative measurement.

109. The system of clause 105, further comprising:

circuitry for performing a comparison using an updated normalcy threshold.

110. The system of clause 105, in which the positioning structure comprises:

the positioning structure mechanically supporting at least a portion of the circuitry for recognizing the pattern in the data from the sensor.

111. The system of clause 95, in which the positioning structure comprises:

clothing.

112. The system of clause 95, in which the positioning structure comprises:

a cuff.

113. The system of clause 95, in which the positioning structure comprises:

a sleeve.

114. The system of clause 95, in which the positioning structure comprises:

a wristband.

115. The system of clause 95, in which the positioning structure comprises:

one or more of eyewear, an earpiece, or a headpiece.

116. The system of clause 95, in which the positioning structure comprises:

the positioning structure configured to surround a portion of the healthcare recipient.

117. The system of clause 95, in which the positioning structure comprises:

the output device configured to receive radio frequency energy as the wireless signal.

118. The system of clause 95, further comprising:

a user interface operable to receive input from the healthcare recipient.

119. The system of clause 118, in which the user interface comprises:

a sonic sensor.

120. The system of clause 118, in which the user interface comprises:

a keypad.

121. The system of clause 118, in which the user interface comprises:

circuitry for presenting content provided by a healthcare facility in the healthcare facility.

122. The system of clause 95, in which the first output device comprises:

circuitry for presenting one or more of a verification or a resource status indication.

123. The system of clause 95, in which the first output device comprises:

circuitry for presenting other information to one or more other recipients.

124. The system of clause 95, in which the first output device comprises:

circuitry for presenting the health-related information with one or more computations of cost.

125. The system of clause 95, in which the first output device comprises:

circuitry for presenting likelihood-indicative data.

126. The system of clause 95, in which the first output device comprises:
circuitry for presenting one or more limb pain indications.

127. The system of clause 95, further comprising:
circuitry for obtaining information indicating a current thermal condition in a peripheral body part of the healthcare recipient.

128. The system of clause 127 in which the circuitry for obtaining information indicating a current thermal condition in a peripheral body part of the healthcare recipient comprises:
circuitry for determining that the information apparently manifests the current thermal condition in the peripheral body part of the healthcare recipient.

129. The system of clause 127 in which the circuitry for obtaining information indicating a current thermal condition in a peripheral body part of the healthcare recipient comprises:
circuitry for extracting a portion of detected information as the information indicating the current thermal condition in the peripheral body part of the healthcare recipient.

130. The system of clause 127 in which the circuitry for obtaining information indicating a current thermal condition in a peripheral body part of the healthcare recipient comprises:
circuitry for obtaining an optical image of the peripheral body part of the healthcare recipient of the information indicating the current thermal condition in the peripheral body part of the healthcare recipient.

131. The system of clause 127 in which the circuitry for obtaining information indicating a current thermal condition in a peripheral body part of the healthcare recipient comprises:
circuitry for detecting that the information indicates normalcy as the current thermal condition in the peripheral body part of the healthcare recipient.

132. The system of clause 127, further comprising:
circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.

133. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for deciding whether to transmit the notification responsive to whether any of the one or more comparisons indicate an abnormal temperature change in the peripheral body part of the healthcare recipient.

134. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision by transmitting the notification to a portable interface.

135. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for ranking a higher-priority destination and a lower-priority destination for the notification.

136. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision whether to transmit the notification partly in response to auditory information from the healthcare recipient.

137. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including auditory data with the notification.

138. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for selecting one or more destinations for the notification.

139. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including thermal-decrease-size-indicative information with the notification.

140. The system of clause 132 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including spatial-size-indicative information with the notification.

141. A system comprising:
a positioning structure configured to be worn by a healthcare recipient;
a receiver supported by the positioning structure and configured to receive a wireless signal; and
a user interaction device supported by the positioning structure and configured to present at least some health-related information in a vicinity of the healthcare recipient responsive to the wireless signal.

142. The system of clause 141, further comprising:
a stationary module operable for transmitting the wireless signal to the receiver.

143. The system of clause 141, further comprising:
circuitry for causing a notification to be routed at least to the user interaction device.

144. The system of clause 141, further comprising:
circuitry for invoking one or more output devices selected in response to a configuration parameter and to the wireless signal.

145. The system of clause 141, further comprising:
circuitry for including at least some medical history data in the health-related information.

146. The system of clause 141, further comprising:
circuitry for including at least some real-time data in the health-related information.

147. The system of clause 141, further comprising:
circuitry for signaling at least a clot-reducing agent in response to an apparent circulatory degradation.

148. The system of clause 141, further comprising:
circuitry for transmitting data indicating one or more concentrations of a nutrient or medication.

149. The system of clause 141, further comprising:
circuitry for detecting thermal data.

150. The system of clause 141, further comprising:
an accelerometer supported by the positioning structure.

151. The system of clause 141, further comprising:
a proximity sensor supported by the positioning structure.

152. The system of clause 141, further comprising:
one or more sensors adjacent a body part of the healthcare recipient.

153. The system of clause 141, further comprising:
a sensor supported by the positioning structure; and
circuitry for recognizing a pattern in data from the sensor.

154. The system of clause 153, further comprising:
circuitry for detecting one or more indications of normalcy in the data from the sensor.

155. The system of clause 153, further comprising:
circuitry for indicating one or more conditional notifications responsive to the data from the sensor.

156. The system of clause 153, further comprising:
circuitry for obtaining a turbulence-indicative auditory value as a flow-change-indicative measurement.

157. The system of clause 153, further comprising:
circuitry for performing a comparison using an updated normalcy threshold.

158. The system of clause 153, in which the positioning structure comprises:
the positioning structure mechanically supporting at least a portion of the circuitry for recognizing the pattern in the data from the sensor.

159. The system of clause 141, in which the positioning structure comprises:
clothing.

160. The system of clause 141, in which the positioning structure comprises:
one or more of a cuff, a sleeve, or a wristband.

161. The system of clause 141, in which the positioning structure comprises:
one or more of eyewear, an earpiece, or a headpiece.

162. The system of clause 141, in which the positioning structure comprises:
the positioning structure configured to surround a portion of the healthcare recipient.

163. The system of clause 141, in which the receiver comprises:
an optical sensor configured to receive optical energy as the wireless signal.

164. The system of clause 141, in which the user interaction device comprises:
a keypad.

165. The system of clause 141, in which the user interaction device comprises:
a touchscreen.

166. The system of clause 141, in which the user interaction device comprises:
circuitry for presenting content provided by a healthcare facility in the healthcare facility.

167. The system of clause 141, in which the user interaction device comprises:
circuitry for presenting one or more of a verification or a resource status indication.

168. The system of clause 141, in which the user interaction device comprises:
circuitry for presenting other information to one or more other recipients.

169. The system of clause 141, in which the user interaction device comprises:
circuitry for presenting the health-related information with one or more computations of cost.

170. The system of clause 141, in which the user interaction device comprises:
circuitry for transmitting likelihood-indicative data.

171. The system of clause 141, in which the user interaction device comprises:
circuitry for transmitting one or more limb pain indications.

172. The system of clause 141, further comprising:
circuitry for obtaining information indicating a current thermal condition in a peripheral body part of the healthcare recipient.

173. The system of clause 172 in which the circuitry for obtaining information indicating a current thermal condition in a peripheral body part of the healthcare recipient comprises:
circuitry for determining that the information apparently manifests the current thermal condition in the peripheral body part of the healthcare recipient.

174. The system of clause 172 in which the circuitry for obtaining information indicating a current thermal condition in a peripheral body part of the healthcare recipient comprises:
circuitry for extracting a portion of detected information as the information indicating the current thermal condition in the peripheral body part of the healthcare recipient.

175. The system of clause 172 in which the circuitry for obtaining information indicating a current thermal condition in a peripheral body part of the healthcare recipient comprises:
circuitry for obtaining an optical image of the peripheral body part of the healthcare recipient of the information indicating the current thermal condition in the peripheral body part of the healthcare recipient.

176. The system of clause 172 in which the circuitry for obtaining information indicating a current thermal condition in a peripheral body part of the healthcare recipient comprises:
circuitry for detecting that the information indicates normalcy as the current thermal condition in the peripheral body part of the healthcare recipient.

177. The system of clause 172, further comprising:
circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.

178. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for deciding whether to transmit the notification responsive to whether any of the one or more comparisons indicate an abnormal temperature change in the peripheral body part of the healthcare recipient.

179. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for signaling the decision by transmitting the notification to a portable interface.

180. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for ranking a higher-priority destination and a lower-priority destination for the notification.

181. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for signaling the decision whether to transmit the notification partly in response to auditory information from the healthcare recipient.

182. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for including auditory data with the notification.

183. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for selecting one or more destinations for the notification.

184. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for including thermal-decrease-size-indicative information with the notification.

185. The system of clause 177 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:

circuitry for including spatial-size-indicative information with the notification.

186. A system comprising:

a positioning structure configured to be worn by a healthcare recipient;

a first output device supported by the positioning structure and configured to transmit at least some health-related information in a vicinity of the healthcare recipient; and a second output device supported by the positioning structure and configured to transmit a wireless signal containing one or more scalar values indicating a position of the healthcare recipient.

187. The system of clause 186, further comprising:

a receiver supported by the positioning structure; and a stationary module operable for transmitting another signal to the receiver.

188. The system of clause 186, further comprising:

circuitry for causing a notification to be routed to at least one of the first output device or the second output device.

189. The system of clause 186, further comprising:

circuitry for invoking at least one of the first output device, the second output device, or a third output device selected in response to a configuration parameter.

190. The system of clause 186, further comprising:

circuitry for including at least some medical history data in the health-related information.

191. The system of clause 186, further comprising:

circuitry for including at least some real-time data in the health-related information.

192. The system of clause 186, further comprising:

circuitry for signaling at least a clot-reducing agent in response to an apparent circulatory degradation.

193. The system of clause 186, further comprising:

circuitry for transmitting data indicating one or more concentrations of a nutrient or medication.

194. The system of clause 186, further comprising:

circuitry for detecting thermal data.

195. The system of clause 186, further comprising:

circuitry for transmitting one or more swelling indications.

196. The system of clause 186, further comprising:

one or more sensors adjacent a body part of the healthcare recipient.

197. The system of clause 186, further comprising:

a sensor supported by the positioning structure and configured to generate sensor data; and circuitry for recognizing a pattern in the sensor data.

198. The system of clause 197, further comprising:

circuitry for detecting one or more indications of normalcy in the sensor data.

199. The system of clause 197, further comprising:

circuitry for indicating one or more conditional notifications responsive to the sensor data.

200. The system of clause 197, further comprising:

circuitry for obtaining a turbulence-indicative auditory value as a flow-change-indicative measurement.

201. The system of clause 197, further comprising:

circuitry for performing a comparison using an updated normalcy threshold.

202. The system of clause 197, in which the positioning structure comprises:
the positioning structure mechanically supporting at least a portion of the circuitry for recognizing the pattern in the sensor data.

203. The system of clause 186, in which the positioning structure comprises:
clothing.

204. The system of clause 186, in which the positioning structure comprises:
one or more of a cuff, a sleeve, or a wristband.

205. The system of clause 186, in which the positioning structure comprises:
one or more of eyewear, an earpiece, or a headpiece.

206. The system of clause 186, in which the positioning structure comprises:
the positioning structure configured to surround a portion of the healthcare recipient.

207. The system of clause 186, further comprising:
a user interface operable to receive input from the healthcare recipient.

208. The system of clause 207, in which the user interface comprises:
a sonic sensor.

209. The system of clause 207, in which the user interface comprises:
a touchscreen.

210. The system of clause 207, in which the user interface comprises:
circuitry for presenting content provided by a healthcare facility in the healthcare facility.

211. The system of clause 186, in which the first output device comprises:
circuitry for transmitting one or more of a verification or a resource status indication.

212. The system of clause 186, in which the first output device comprises:
circuitry for presenting other information to one or more other recipients.

213. The system of clause 186, in which the first output device comprises:
circuitry for transmitting the health-related information with one or more computations of cost.

214. The system of clause 186, in which the first output device comprises:
circuitry for transmitting likelihood-indicative data.

215. The system of clause 186, further comprising:
circuitry for obtaining information indicating a current thermal condition in a peripheral body part of the healthcare recipient.

216. The system of clause 215 in which the circuitry for obtaining information indicating a current thermal condition in a peripheral body part of the healthcare recipient comprises:
circuitry for determining that the information apparently manifests the current thermal condition in the peripheral body part of the healthcare recipient.

217. The system of clause 215 in which the circuitry for obtaining information indicating a current thermal condition in a peripheral body part of the healthcare recipient comprises:
circuitry for extracting a portion of detected information as the information indicating the current thermal condition in the peripheral body part of the healthcare recipient.

218. The system of clause 215 in which the circuitry for obtaining information indicating a current thermal condition in a peripheral body part of the healthcare recipient comprises:
circuitry for obtaining an optical image of the peripheral body part of the healthcare recipient of the information indicating the current thermal condition in the peripheral body part of the healthcare recipient.

219. The system of clause 215 in which the circuitry for obtaining information indicating a current thermal condition in a peripheral body part of the healthcare recipient comprises:
circuitry for detecting that the information indicates normalcy as the current thermal condition in the peripheral body part of the healthcare recipient.

220. The system of clause 215, further comprising:
circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.

221. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for deciding whether to transmit the notification responsive to whether any of the one or more comparisons indicate an abnormal temperature change in the peripheral body part of the healthcare recipient.

222. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision by transmitting the notification to a portable interface.

223. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for ranking a higher-priority destination and a lower-priority destination for the notification.

224. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for signaling the decision whether to transmit the notification partly in response to auditory information from the healthcare recipient.

225. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including auditory data with the notification.

226. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for selecting one or more destinations for the notification.

227. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including thermal-decrease-size-indicative information with the notification.

228. The system of clause 220 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
circuitry for including spatial-size-indicative information with the notification.

Although selected combinations of the respective clauses are indicated above, this is by way of illustration only, and all relevant combinations of the clauses is also envisaged herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
first means for receiving a wireless signal;
second means for presenting at least some health-related information in a vicinity of a healthcare recipient responsive to the wireless signal;
wearable means for positioning the first means and the second means in relation to the healthcare recipient; and
means for including at least some medical history data in the health-related information.

2. A system comprising:
a positioning structure configured to be worn by a healthcare recipient;
a receiver supported by the positioning structure and configured to receive a wireless signal;
a user interaction device supported by the positioning structure and configured to present at least some health-related information in a vicinity of the healthcare recipient responsive to the wireless signal; and
circuitry for including at least some medical history data in the health-related information.

3. The system of claim 2, further comprising:
a stationary module operable for transmitting the wireless signal to the receiver.

4. The system of claim 2, further comprising:
circuitry for causing a notification to be routed at least to the user interaction device.

5. The system of claim 2, further comprising:
circuitry for invoking one or more output devices selected in response to a configuration parameter and to the wireless signal.

6. The system of claim 2, further comprising:
circuitry for including at least some real-time data in the health-related information.

7. The system of claim 2, further comprising:
circuitry for signaling at least a clot-reducing agent in response to an apparent circulatory degradation.

8. The system of claim 2, further comprising:
circuitry for transmitting data indicating one or more concentrations of a nutrient or medication.

9. The system of claim 2, further comprising:
circuitry for detecting thermal data.

10. The system of claim 2, further comprising:
an accelerometer supported by the positioning structure.

11. The system of claim 2, further comprising:
a proximity sensor supported by the positioning structure.

12. The system of claim 2, further comprising:
one or more sensors adjacent a body part of the healthcare recipient.

13. The system of claim 2, further comprising:
a sensor supported by the positioning structure; and
circuitry for recognizing a pattern in data from the sensor.

14. The system of claim 13, further comprising:
circuitry for detecting one or more indications of normalcy in the data from the sensor.

15. The system of claim 13, further comprising:
circuitry for indicating one or more conditional notifications responsive to the data from the sensor.

16. The system of claim 13, further comprising:
circuitry for performing a comparison using an updated normalcy threshold.

17. The system of claim 2, in which the positioning structure comprises:
clothing.

18. The system of claim 2, in which the positioning structure comprises:
one or more of a cuff, a sleeve, or a wristband.

19. The system of claim 2, in which the positioning structure comprises:
one or more of eyewear, an earpiece, or a headpiece.

20. The system of claim 2, in which the positioning structure comprises:
the positioning structure configured to surround a portion of the healthcare recipient.

21. The system of claim 2, in which the receiver comprises:
an optical sensor configured to receive optical energy as the wireless signal.

22. The system of claim 2, in which the user interaction device comprises:
a keypad.

23. The system of claim 2, in which the user interaction device comprises:
a touchscreen.

24. The system of claim 2, in which the user interaction device comprises:
circuitry for presenting content provided by a healthcare facility in the healthcare facility.

25. The system of claim 2, in which the user interaction device comprises:
circuitry for presenting one or more of a verification or a resource status indication.

26. The system of claim 2, in which the user interaction device comprises:
circuitry for presenting other information to one or more other recipients.

27. The system of claim 2, in which the user interaction device comprises:
- circuitry for transmitting likelihood-indicative data.

28. The system of claim 2, further comprising:
- circuitry for obtaining information indicating a current thermal condition in a peripheral body part of the healthcare recipient.

29. The system of claim 28 in which the circuitry for obtaining information indicating a current thermal condition in a peripheral body part of the healthcare recipient comprises:
- circuitry for determining that the information apparently manifests the current thermal condition in the peripheral body part of the healthcare recipient.

30. The system of claim 28 in which the circuitry for obtaining information indicating a current thermal condition in a peripheral body part of the healthcare recipient comprises:
- circuitry for extracting a portion of detected information as the information indicating the current thermal condition in the peripheral body part of the healthcare recipient.

31. The system of claim 28 in which the circuitry for obtaining information indicating a current thermal condition in a peripheral body part of the healthcare recipient comprises:
- circuitry for obtaining an optical image of the peripheral body part of the healthcare recipient of the information indicating the current thermal condition in the peripheral body part of the healthcare recipient.

32. The system of claim 28, further comprising:
- circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient.

33. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for deciding whether to transmit the notification responsive to whether any of the one or more comparisons indicate an abnormal temperature change in the peripheral body part of the healthcare recipient.

34. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for ranking a higher-priority destination and a lower-priority destination for the notification.

35. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for signaling the decision whether to transmit the notification partly in response to auditory information from the healthcare recipient.

36. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for including auditory data with the notification.

37. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for selecting one or more destinations for the notification.

38. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for including thermal-decrease-size-indicative information with the notification.

39. The system of claim 32 in which the circuitry for signaling a decision whether to transmit a notification at least partly in response to one or more comparisons between the information indicating the current thermal condition in the peripheral body part of the healthcare recipient and information indicating a prior thermal condition in the peripheral body part of the healthcare recipient comprises:
- circuitry for including spatial-size-indicative information with the notification.

* * * * *